United States Patent
Kim et al.

(10) Patent No.: US 9,481,866 B2
(45) Date of Patent: Nov. 1, 2016

(54) METHODS OF PRODUCING T CELL POPULATIONS ENRICHED FOR STABLE REGULATORY T-CELLS

(71) Applicant: The United States of America, as represented by the Secretary, Department of Health and Human Services, Washington, DC (US)

(72) Inventors: Yong Chan Kim, Rockville, MD (US); Ethan Shevach, Rockville, MD (US)

(73) Assignee: The United States of America, as represented by the Secretary, Department of Health and Human Services, Washington, DC (US)

(*) Notice: Subject to any disclaimer, the term of this patent is extended or adjusted under 35 U.S.C. 154(b) by 73 days.

(21) Appl. No.: 13/716,900

(22) Filed: Dec. 17, 2012

(65) Prior Publication Data

US 2013/0157363 A1 Jun. 20, 2013

Related U.S. Application Data

(60) Provisional application No. 61/576,837, filed on Dec. 16, 2011.

(51) Int. Cl.
*C12N 5/00* (2006.01)
*C12N 5/02* (2006.01)
*C12N 5/071* (2010.01)
*C12N 5/0783* (2010.01)

(52) U.S. Cl.
CPC ........... *C12N 5/0636* (2013.01); *C12N 5/0637* (2013.01)

(58) Field of Classification Search
None
See application file for complete search history.

(56) References Cited

U.S. PATENT DOCUMENTS

2003/0147865 A1* 8/2003 Salomon et al. .......... 424/93.21

OTHER PUBLICATIONS

Life technologies, 2014, silencer Negative control No. 1 siRNA. pp. 1-2.*
Wei et al., 2006, Blood. vol. 108: 426-31.*
Chiffoleau et al., 2007, vol. 19: 193-201.*
Getnet et al., Mar. 2010, Mol. Immunol. vol. 47: 1595-1600.*
Keever-Taylor et al., 2007, Cytotherapy, vol. 9: 144-157.*
Hoffmann et al., 2004, Blood vol. 104: 895-903.*
Kim et al., 2012, Blood, vol. 119: 2810-2818.*
Golovina et al., 2008, J. Immunol. vol. 181: 2855-2868.*
Brunstein, C.G., et al., "Infusion of ex vivo expanded T regulatory cells in adults transplanted with umbilical cord blood: safety profile and detection kinetics," *Blood*, 2011, 117(3):1061-1070.

Chen, Q., et al., "IL-2 controls the stability of Foxp3 expression in TGF-beta-induced Foxp3+ T cells in viv," *J Immunol.*, 2011, 86(11):6329-6337.
Di Ianni, M., et al., "Tregs prevent GVHD and promote immune reconstitution in HLA-haploidentical transplantation," *Blood*, 2011, 117(14):3921-3928.
Floess, S, et al. "Epigenetic control of the foxp3 locus in regulatory T cells," *PLoS Biol*, 2007, 5(2):e38.
Golovina, T.N., "Retinoic Acid and Rapamycin Differentially Affect and Synergistically Promote the Ex Vivo Expansion of Natural Human T Regulatory Cells," PLoS One, 2011;6(1):e15868.
Hippen, K.L., et al., "Generation and Large-Scale Expansion of Human Inducible Regulatory T Cells That Suppress Graft-Versus-Host Disease," *American Journal of Transplantation*, 2011, 11(6):1148-1157.
Hippen, K.L., et al., "Massive ex Vivo Expansion of Human Natural Regulatory T Cells (Tregs) with Minimal Loss of in Vivo Functional Activity." Science Translational Medicine, 2011, 3(83):83ra41-83ra41.
Hoffmann, P., "Donor-type CD4(+)CD25(+) regulatory T cells suppress lethal acute graft-versus-host disease after allogeneic bone marrow transplantation," *J Exp Med*, 2002, 196(3):389-399.
Hoffmann, P., et al., "Loss of FOXP3 expression in natural human CD4+CD25+ regulatory T cells upon repetitive in vitro stimulation," *Eur J Immunol*, 2009, 39(4):1088-1097.
Hoffmann, P., et al., "Only the CD45RA+ subpopulation of CD4+CD25high T cells gives rise to homogeneous regulatory T-cell lines upon in vitro expansion," *Blood*, 2006, 108(13):4260-4267.
Liu, H., et al., "Toll-like receptor 2 signaling modulates the functions of CD4+ CD25+ regulatory T cells," *Proc Nati Acad Sci USA*, 2006, 03(18):7048-7053.
Liu, W, et al., "CD127 expression inversely correlates with FoxP3 and suppressive function of human CD4+ T reg cells," *J Exp Med*, 2006, 203(7):1701-1711.
McClymont, S.A., "Plasticity of human regulatory T cells in healthy subjects and patients with type 1 diabetes," J Immunol, 2011, 186(7):3918-3926.
Miyara, M., et al., "Functional Delineation and Differentiation Dynamics of Human CD4+ T Cells Expressing the FoxP3 Transcription Factor,." *Immunity*, 2009,30(6):899-911.
Peng, G., et al., "Toll-like receptor 8-mediated reversal of CD4+ regulatory T cell function," *Science*, 2005, 309(5739):1380-1384.
Peters, J.H., et al., "Clinical grade Treg: GMP isolation, improvement of purity by CD127 Depletion, Treg expansion, and Treg cryopreservation," PLoS One, 2008, 3(9):e3161.

(Continued)

*Primary Examiner* — Amy Juedes
(74) *Attorney, Agent, or Firm* — Sheridan Ross P.C.

(57) ABSTRACT

The present invention provides methods for producing cell populations enriched for stable, regulatory T cells (Tregs). In particular, the invention relates to methods for culturing T cells such that the final culture is enriched for stable, regulatory T cells. It also relates to methods for stabilizing regulatory T cells. Also provided are compositions enriched for stable, regulatory T cells, which are useful for treating individuals in need of such treatment. The methods and compositions disclosed herein can also be used to treat an individual suffering from an immune-mediated disease.

15 Claims, 12 Drawing Sheets

(56) References Cited

OTHER PUBLICATIONS

Polansky, et al., "Methylation matters: binding of Ets-1 to the demethylated Foxp3 gene contributes to the stabilization of Foxp3 expression in regulatory T cells," *J Mol Med*, 2010,88:1029-1040.
Riley, J.L., et al., "Human T regulatory cell therapy: take a billion or so and call me in the morning," *Immunity*, 2009, 30(5):656-665.
Roncarolo, M-G, et al., "Regulatory T-cell immunotherapy for tolerance to self antigens and alloantigens in humans," *Nat Rev Immunol*, 2007, 7(8):585-598.
Shevach, E.M., "Mechanisms of foxp3+ T regulatory cell-mediated suppression," *Immunity*, 2009, 30(5):636-645.
Shevach, E.M., et al., "The critical contribution of TGF-beta to the induction of Foxp3 expression and regulatory T cell function," *Eur J Immunol*, 2008, 38(4):915-917.
Thornton, A.M., et al., "Expression of Helios, an Ikaros transcription factor family member, differentiates thymic-derived from peripherally induced Foxp3+ T regulatory cells," *J Immunol*, 2010,184(7):3433-3441.
Trzonkowski, P., et al., "First-in-man clinical results of the treatment of patients with graft versus host disease with human ex vivo expanded CD4+CD25+CD127—T regulatory cells," *Clin Immunol*, 2009, 133(1):22-26.

* cited by examiner

METHODS OF PRODUCING T CELL POPULATIONS ENRICHED FOR STABLE REGULATORY T-CELLS

CROSS-REFERENCE TO RELATED APPLICATION

This application is a non-provisional patent application which claims the benefit under 35 U.S.C. 119(e) of U.S. Provisional Patent Application Ser. No. 61/576,837, filed Dec. 16, 2011, entitled "METHODS OF PRODUCING T CELL POPULATIONS ENRICHED FOR STABLE REGULATORY T-CELLS," the disclosure of which is hereby incorporated herein by reference in its entirety.

FIELD OF INVENTION

The present invention relates to methods of producing compositions that are enriched for regulatory T-cells, and the use of such compositions in treating disease.

BACKGROUND

Foxp3$^+$ Tregs are a unique subset of CD4$^+$ T cells responsible for self-tolerance and for the prevention of autoimmune disease (Shevach E M, *Immunity*, 2009; 30(5): 636-645). Adoptive Treg infusion has been suggested as a potential therapy for the prevention of Graft versus Host Disease (GVHD) following stem cell transplantation, organ allograft rejection, and for the treatment of autoimmune diseases such as type I diabetes and multiple sclerosis (Roncarolo M-G, Battaglia M., *Nat Rev Immuno.*, 2007; 7(8):585-598; Riley J L, June C H, Blazar B R, Immunity, 2009; 30(5):656-665). Adoptive transfer of Foxp3$^+$ Tregs in mouse models has been shown to prevent acute and chronic GVHD without negative effects on the graft versus leukemia response (Hoffmann P, Ermann J, Edinger M, Fathman C G, Strober S, *J Exp Med*, 2002; 196(3):389-399). More recently, a number of groups have reported that co-transfer of expanded Tregs from umbilical cord samples (Brunstein C G, Miller J S, Cao Q, et al., *Blood*, 2011; 117(3):1061-1070) or from peripheral blood appears to be both safe (Trzonkowski P, Bieniaszewska M, Jukinska J, et al., *Clin Immunol*, 2009; 133(1):22-26) and in one study remarkably effective in preventing acute GVHD following stem cell transplantation (Di Ianni M, Falzetti F, Carotti A, et al., *Blood*, 2011; 117(14):3921-3928).

Although considerable enthusiasm has been generated for adoptive Treg therapy, several major issues remain to be resolved. First, most clinical applications of Treg therapy will require large numbers of cells and optimal methods for Treg expansion are now being explored. Expansion of highly purified populations of human Tregs also frequently results in loss of Foxp3 expression during the expansion process. Secondly, in contrast to studies in the mouse, Foxp3 expression can be readily induced during in vitro stimulation of conventional human T cells (Shevach E M, Tran D Q, Davidson T S, Andersson J, *Eur J Immunol*, 2008; 38(4): 915-917). T cells induced in vitro to express Foxp3 frequently lack a Treg phenotype, continue to make effector cytokines and lack in vitro suppressive function (Shevach E M, Tran D Q, Davidson T S, Andersson J, *Eur J Immunol*, 2008; 38(4):915-917). Thus, expression of Foxp3 cannot be considered a completely reliable marker for functional human Tregs.

A number of approaches have been used to address these problems. Combined use of several surface markers (CD127$^{lo}$ and CD25$^{hi}$) has facilitated isolation of more highly enriched populations of Foxp3$^+$ T cells with less contamination by CD25$^{int}$ activated T cells (Liu W, Putnam A L, Xu-Yu Z, et al., *J Exp Med.* 2006; 203(7):1701-1711). Addition of inhibitors of the mTOR pathway, such as rapamycin, block the expansion of contaminating conventional T cells and favor the expansion of Tregs, but purity greater than 60% is rarely achieved after several rounds of expansion depending on the starting population (Hippen K L, Merkel S C, Schirm D K, et al., *American Journal of Transplantation*, 2011; 11(6): 1148-1157). CD4$^+$CD25$^+$CD45RA$^+$Foxp3$^+$ T cells, although a minor subpopulation (5-30%) of the Foxp3$^+$ pool in adults, appear to have a greater propensity to expand in culture and have enhanced stability of Foxp3 expression compared to CD4$^+$CD25$^+$CD45RO$^+$Foxp3$^+$ T cells (Miyara M, Yoshioka Y, Kitoh A, et al., *Immunity*, 2009; 30(6):899-911).

Foxp3$^+$ Tregs can be divided into two potentially distinct subpopulations. One population is generated in the thymus and has been termed natural (n)Tregs. A second population is generated extrathymically in peripheral sites and has been termed induced (i) Tregs or adaptive Treg. It has recently (Thornton A M, Korty P E, Tran D Q, et al., *J. Immunol.* 2010; 184(7):3433-3441) been demonstrated that the transcription factor, Helios, a member of the Ikaros gene superfamily, is expressed in 70% of both mouse and human Foxp3$^+$ T cells. Foxp3$^+$ Helios$^-$ T cells are primarily iTregs as Foxp3$^+$ T cells induced in vitro are Helios$^-$, and Foxp3$^+$ T cells induced in vivo in response to oral antigen administration, antigen administered i.v., or T cells activated in response to lymphopenia are almost exclusively Helios$^-$.

Currently, there is no reliable method for producing populations of functional, human Tregs that can be used for treating disease. The present invention provides such a method.

SUMMARY OF INVENTION

The present invention relates to a method for producing a population of cells enriched for stable, regulatory T cells. In one embodiment, the method comprises culturing isolated cells comprising an initial population of regulatory T-cells, in the presence of an oligonucleotide, to expand the initial regulatory T-cells. In one embodiment, the oligonucleotide is an oligodeoxynucleotide. In one embodiment, the oligonucleotide is between 11 and 49 nucleotides in length. In one embodiment, the oligonucleotide is between 15 and 40 nucleotides in length. In one embodiment, the oligonucleotide is between 20 and 30 nucleotides in length. In a preferred embodiment, the oligonucleotide is 25 nucleotides in length.

In one embodiment, the method is conducted using isolated peripheral blood mononuclear cells. In a further embodiment, the isolated cells are lymphocytes. In a further embodiment, at least some of the isolated cells are CD4+ Foxp3+. In yet a further embodiment, the isolated cells are also Helios+. In one embodiment, at least some of the isolated cells have a characteristic selected from the group consisting of being CD4 positive, being CD25$^{hi}$, and being CD127$^-$. In a further embodiment, at least some of the isolated cells have a characteristic selected from the group consisting of being Foxp3 positive and being Helios positive.

In one embodiment, expansion of the initial regulatory T-cells results in a population of cells in which at least 60% of the cells are stable, regulatory T-cells. In one embodiment, expansion of the initial regulatory T-cells results in a population of cells in which at least 70% of the cells are stable, regulatory T-cells. In one embodiment, expansion of the initial regulatory T-cells results in a population of cells in which at least 80% of the cells are stable, regulatory T-cells. In one embodiment, expansion of the initial regulatory T-cells results in a population of cells in which at least 90% of the cells are stable, regulatory T-cells. In one embodiment, expansion of the initial regulatory T-cells results in a population of cells in which at least 95% of the cells are stable, regulatory T-cells.

Another embodiment of the present invention is a method for stabilizing T regulatory cells. In one embodiment, the method comprises culturing isolated cells comprising an initial population of regulatory T-cells, in the presence of an oligonucleotide to expand the initial regulatory T-cells.

Another embodiment of the present invention is a composition comprising isolated cells, wherein at least 60% of the isolated cells are stable, regulatory T-cells. In one embodiment, composition is produced by culturing isolated cells comprising an initial population of regulatory T-cells, in the presence of an oligonucleotide to expand the initial regulatory T-cells. In one embodiment, the stable, regulatory T-cells are Foxp3+ Helios+.

Another embodiment of the present invention is a method for treating an individual for an autoimmune disease, the method comprising administering a composition comprising isolated cells, wherein at least 60% of the isolated cells are stable, regulatory T-cells. In one embodiment, composition is produced by culturing isolated cells comprising an initial population of regulatory T-cells, in the presence of an oligonucleotide to expand the initial regulatory T-cells. In one embodiment, the stable, regulatory T-cells are Foxp3+ Helios+.

CD4$^+$CD25$^+$ Tregs were isolated from a male donor and were expanded with anti-CD3/CD28 for 9 days. The cells were then fixed and stained with anti-Foxp3 and anti-Helios. The 4 different subsets (Foxp3$^+$Helios$^+$, Foxp3$^+$Helios$^-$, Foxp3$^-$Helios$^+$, Foxp3Helios$^-$) were sorted (left plot). Extraction of genomic DNA and reading the methylation status of the TSDR was performed as described in Methods. Each bar indicates percent methylation (mean±SD) of the 11 CpGs analyzed.

Figure 9:
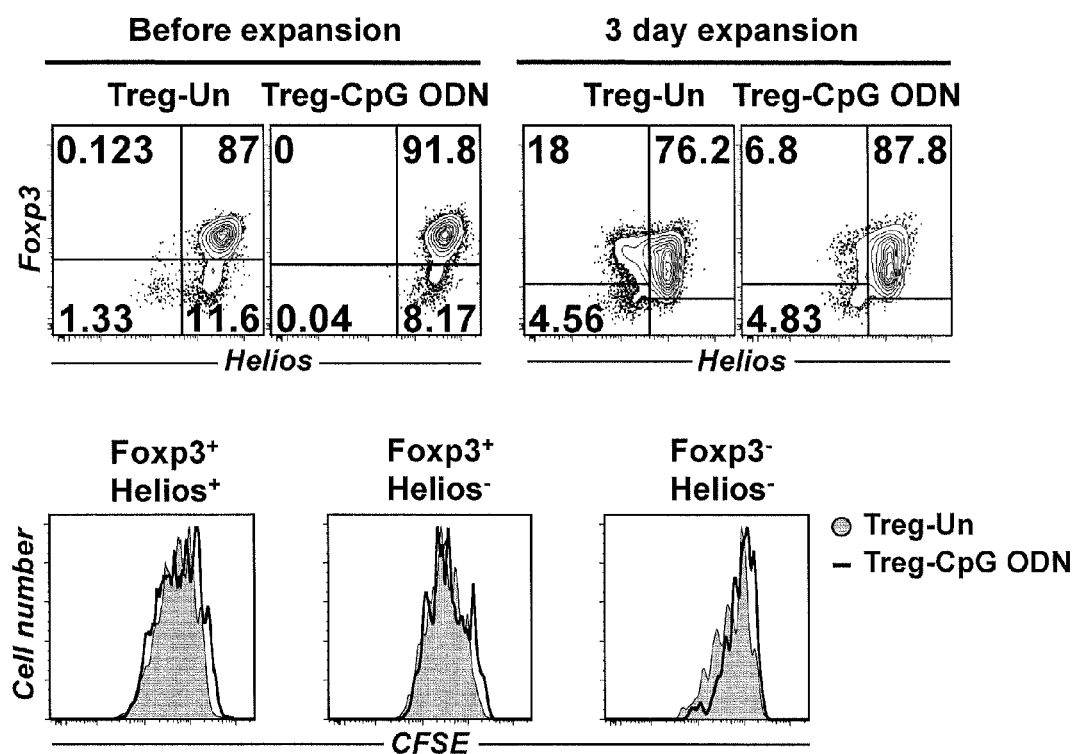

FIG. 9. Effect of Initial CpG ODN Treatment on the Subsequent Proliferative Responses of Treg Subpopulations in the Absence of ODN. Tregs (CD4$^+$CD127$^{lo}$CD25$^+$ CD45RA$^+$) were isolated and stimulated for 5 days in the presence or absence of CpG ODN (2.5 μM). Stimulated cells were washed twice in complete media, and labeled with CFSE. CFSE-labeled cells (Foxp3$^+$Helios$^+$, Foxp3$^+$Helios$^-$, and Foxp3$^-$Helios$^-$) were then stimulated with anti-CD3/CD28 beads for 3 more days in the absence of ODNs and their proliferative responses measured by CFSE dilution. Left top plots shows Foxp3 and Helios expression after the initial 5 day-expansion. Right top plots show Foxp3 and Helios expression after the second stimulation in the absence of CpG ODN. Left bottom histogram indicates CFSE labeling of each population before second culture. Right three bottom histograms show the CFSE dilution plots of each subpopulation after the second 3-day culture in the absence of the ODN.

Figure 10:
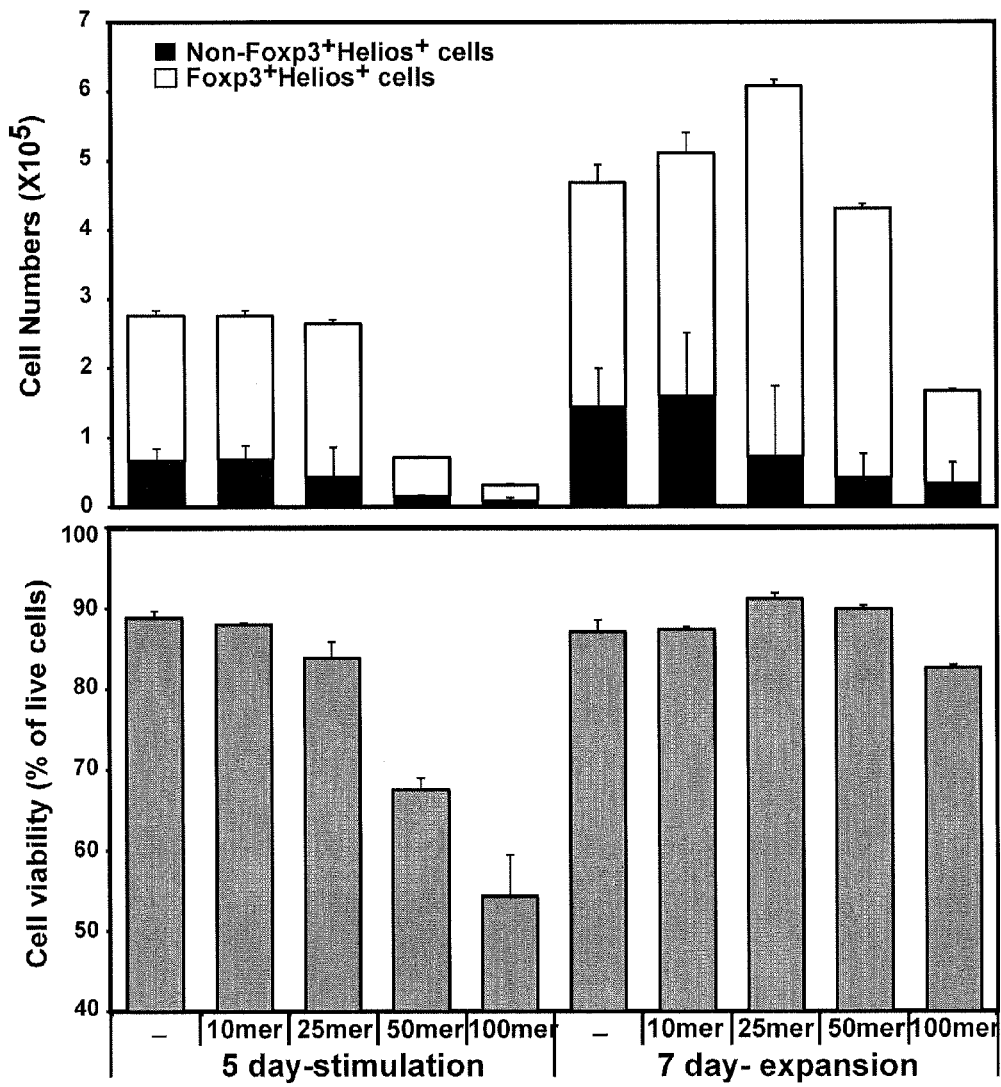

FIG. 10. Effect of ODNs of Different Length on Stabilization of Foxp3 Expression.

Figure 6:
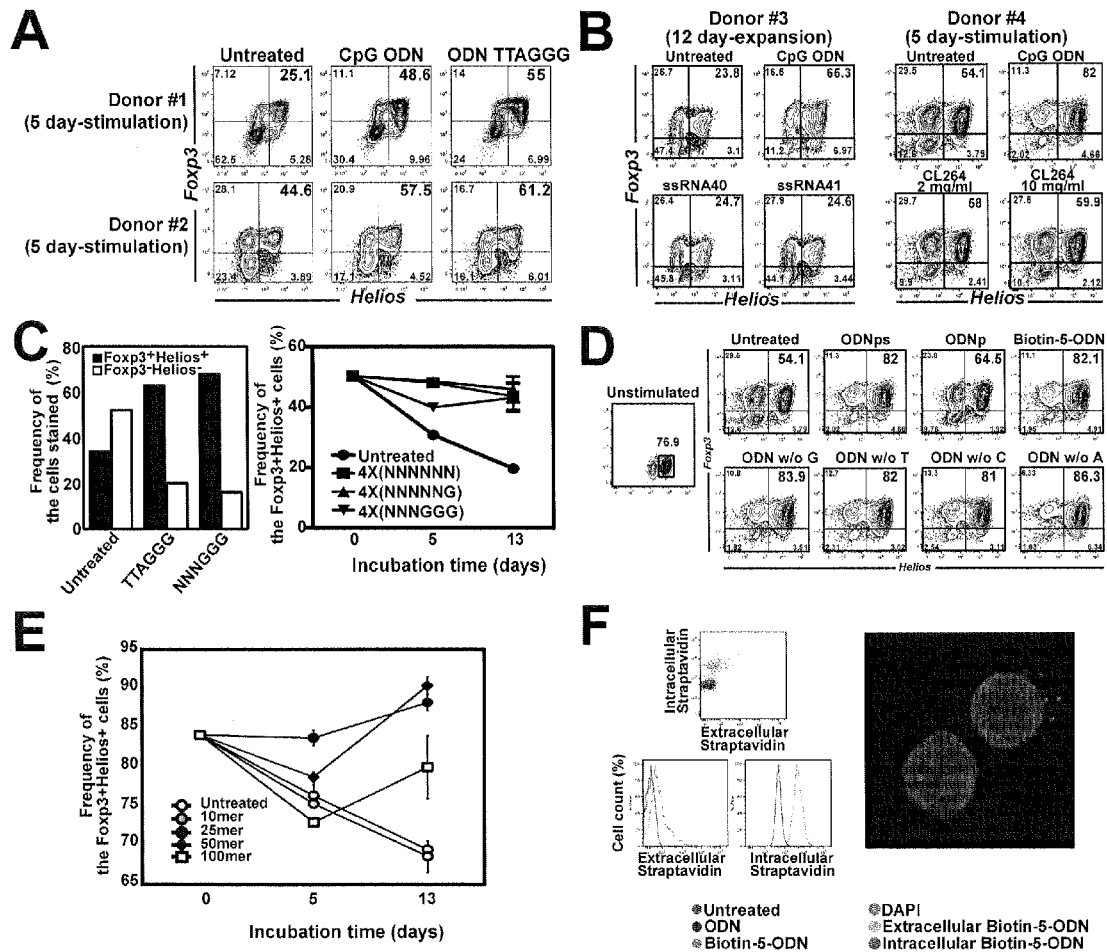
FIG. 6. Random ODNs Also Stabilize Foxp3$^+$Helios$^+$ T Cells. (A) Both a TLR9 agonist and a TLR9 antagonist stabilize Helios$^+$ Foxp3$^+$ Tregs. Cells were isolated as in FIG. 5 and stimulated cells in the presence of 2.5 μM CpG ODN or ODN TTAGGG for the indicated time. (B) TLR7 and TLR8 agonists do not stabilize Helios$^+$Foxp3$^+$ Tregs. Cells were isolated as in panel a and stimulated in the presence of CpG ODN, or 10 μM of ssDNA40 (CL264, TLR8 agonist) or ssDNA40 (TLR7 agonist) or ssRNA41 (negative control for ssDNA40). (C) Random sequence ODNs stabilize Helios Foxp3$^+$ Tregs. Left panel, CD4$^+$CD127$^{lo}$CD25$^+$ cells were sorted and stimulated for 5 days in the presence of 2.5 μM of ODN TTAGGG or ODN NNNGGG. The cells were then expanded with anti-CD3/CD28 beads in the absence of the ODN and stained for Foxp3 and Helios expression 8 days later. Right panel, same conditions as in left panel except that different ODNs were added (4× indicates 4-times repeat (24 mers) of 6 by nucleotides). (D) Stabilization of Foxp3 and Helios expression by ODN requires physical stability of the ODN, but no specific base composition. CD4$^+$CD127$^{lo}$CD25$^{hi}$ cells were stimulated and expanded as same as panel (C) in the presence of phosphorothioate backboned ODN (ODNps), phosphodiester backboned ODN (ODNp), biotin-conjugated ODN at 5' end (Biotin-5-ODN), or ODNs w/o N (G, A, T, or C), indicating randomly synthesized ODN with exclusion of N nucleotide (G, A, T, or C). All ODNs used are 24mers at a concentration of 2.5 μM. (E) ~25 base-pair ODNs are optimal for stabilization of Foxp3 and Helios expression. CD4$^+$CD127$^{lo}$CD25$^+$ cells were isolated as in panel (A), stimulated for 5 days in the presence of different length ODNs (10mer, 10-bp long ODN; 25mer, 25-bp long ODN; 50mer, 50-bp long ODN; 100mer, 100-bp long ODN). Simulated cells were expanded for an additional 12 days in the absence of the ODN were treated during 5 day of stimulation, then, stimulated cells were expanded for 7 more days in the absence of ODNs, and stained for Foxp3 and Helios expression. Data shown is the one of 4 independent experiments. (F) ODNs are localized in cytosol of Tregs. MACS-sorted CD4$^+$ T cells were isolated from buffy coat, stimulated with plate-bound anti-CD3/CD28 for 18 hours in the presence of Biotin-5-ODN or unlabeled ODN and then washed 3 times in FACS staining buffer. Extra- and intracellular Biotin-5-ODN in stimulated cells was stained with different fluorescence-conjugated strepavidins. For the microscopic analysis, fixed and stained cells were mounted with DAPI-containing mounting solution (scale 200×).

Experiment was performed as described in FIG. 6e. Top graph indicates the total cells recovered (mean±SD) from cultures in the presence of the ODN. Bottom graph indicates the percent (mean±SD) of viable cells in the same cultures. Similar results were obtained with cells isolated from 3 different donors.

Figure 11:
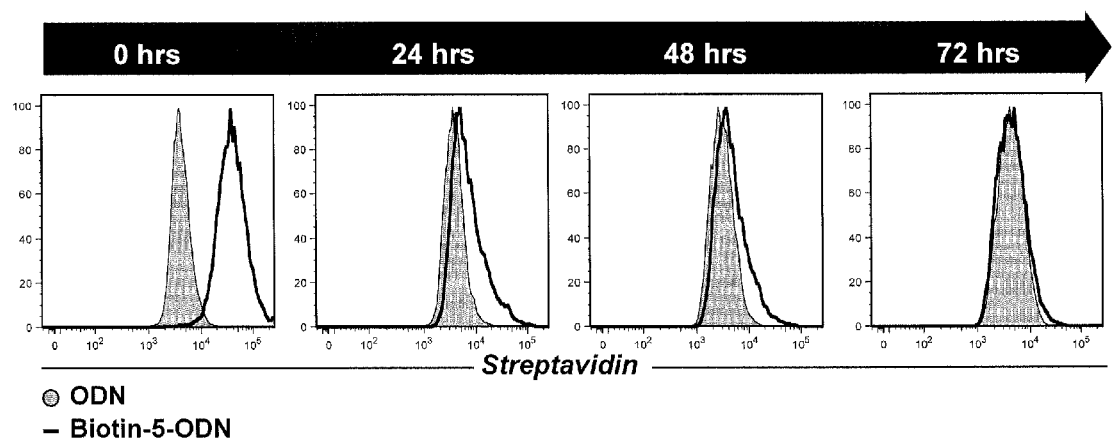

FIG. 11. ODN Cannot be Detected in Foxp3+Helios+ Cells after 72 Hours of Expansion in the Absence of ODN. CD4$^+$CD127$^-$CD25$^{hi}$ cells were isolated and stimulated for days in the presence of ODN (2.5 μM). Stimulated cells were washed in fresh culture media twice and resuspended in IL-2 containing media and expanded in the absence of ODN. At the indicated time, expanded cells were harvested, fixed, permeabilized, and stained with Biotin-conjugated ODN and FITC-Streptavidin. The result is one of three experiments with cells from different donors.

Figure 12:
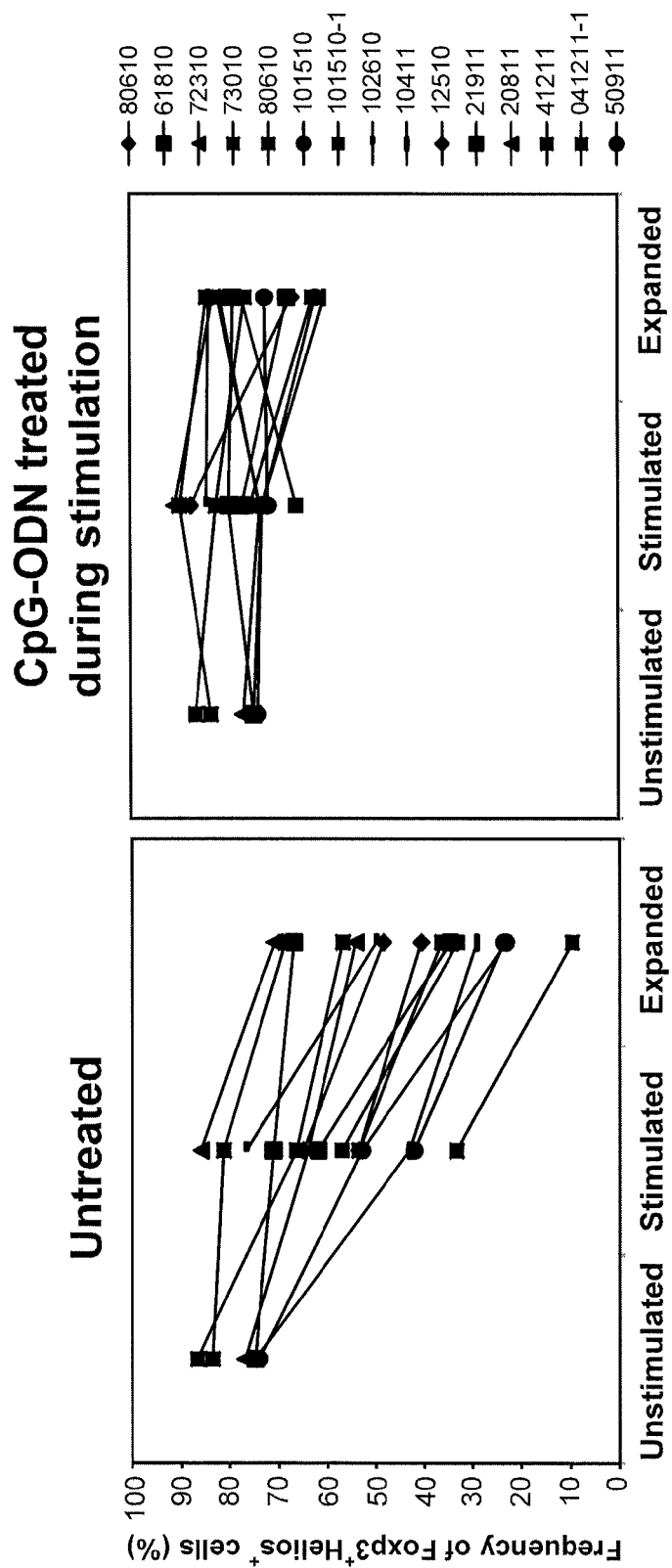

FIG. 12. Stabilization effect of ODN is consistently observed across individuals regardless and is independent of age. FACS-sorted CD4$^+$CD25$^+$ cells (square gate in left plot) were stimulated with plate-bound anti-CD3 and anti-CD28 in the presence of ODN (ODN2395 or custom-synthesized ODN, 2.5 μM) for 5 days. The cells were then washed and incubated for two additional 7 days in IL-2 containing media. Foxp3 and Helios staining was performed on gated viable CD4$^+$ cells. Donors (n=15) ranged in age from 19-75 and were all male.

DETAILED DESCRIPTION OF THE INVENTION

The present invention relates to a novel method for producing T cells that are useful for treating diseases related to the immune system. More specifically, the present invention relates to the inventor's discovery that the presence of oligodeoxynucleotides (ODNs) having particular properties, during expansion of certain lymphocyte populations in cell culture, results in an expanded cell population that is enriched for regulatory T cells (Tregs). Such populations of cells are useful for preventing or treating disease such as Graft versus host Disease (GVHD) and autoimmune diseases such as, for example, type I diabetes and multiple sclerosis.

Before the present invention is further described, it is to be understood that this invention is not strictly limited to particular embodiments described, as such may of course vary. It is also to be understood that the terminology used herein is for the purpose of describing particular embodiments only, and is not intended to be limiting, since the scope of the present invention will be limited only by the claims.

It must be noted that as used herein and in the appended claims, the singular forms "a," "an," and "the" include plural referents unless the context clearly dictates otherwise. It should further be understood that as used herein, the term "a" entity or "an" entity refers to one or more of that entity. For example, a nucleic acid molecule refers to one or more nucleic acid molecules. As such, the terms "a", "an", "one or more" and "at least one" can be used interchangeably. Similarly the terms "comprising", "including" and "having" can be used interchangeably.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed. In addition, all sub-combinations are also specifically embraced by the present invention and are disclosed herein just as if each and every such sub-combination was individually and explicitly disclosed herein.

It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Methods of the present invention can generally be practiced by culturing isolated cells that comprise a population of T-cells, in the presence of an oligonucleotide having particular characteristics, to expand at least a portion of the T-cell population. In preferred embodiments, the isolated cells comprise an initial population of regulatory T-cells, and the culture conditions result in expansion of at least a portion of the initial regulatory T-cells. The result of such methods is an expanded population of cells that is enriched for stable, regulatory T-cells. These enriched cells can be used to treat disease related to the immune system.

Accordingly, one embodiment of the present invention is a method to produce a population of cells having stable, regulatory T-cells (Tregs), the method comprising isolating cells comprising an initial population of regulatory T-cells, and culturing the isolated cells in the presence of an oligonucleotide having particular characteristics, to expand at least some of the initial, regulatory T-cells.

As used herein, the terms isolated, isolating, purified, and the like, do not necessarily refer to the degree of purity of a cell or molecule of the present invention. Such terms instead refer to cells or molecules that have been separated from their natural milieu or from components of the environment in which they are produced. For example, a naturally occurring cell or molecule (e.g., a T cell, a DNA molecule, etc.) present in a living animal, including humans, is not isolated. However, the same cell, or molecule, separated from some or all of the coexisting materials in the animal, is considered isolated. As a further example, according to the present invention, cells that are present in a sample of blood obtained from a person would be considered isolated. It should be appreciated that cells obtained from such a sample using further purification steps would also be referred to as isolated, in keeping with the notion that isolated does not refer to the degree of purity of the cells.

With further regard to the present invention, isolated cells useful for practicing the disclosed methods can be any isolated cells that comprise T-cells, and in particular, regulatory T-cells. Such cells can be obtained as a sample from an animal, including humans, or they can be obtained from cells in culture. Examples of cell samples useful for practicing the present invention include, but are not limited to, blood samples, lymph samples, and tissue samples. In one embodiment, the isolated cells are obtained from a blood sample. In another embodiment, the isolated cells are obtained from cells in culture.

It is known in the art that T-cells belong to the class of cells known as lymphocytes, which are a type of agranulocyte. Agranulocytes, also known as mononuclear leukocytes, are characterized by the absence of granules in their cytoplasm. The lymphocytes comprise at least three separate cell types: B-cells, T-cells and natural killer cells. Furthermore, T-cells can be further divided into effector T cells and regulatory T-cells. In various embodiments, the isolated cells can comprise mononuclear, agranulocyte or lymphocyte cell populations, so long as they comprise T-cells, and in particular, regulatory T-cells (also referred to as Tregs). As used herein, Tregs are a subpopulation of T-cells that suppress activation of the immune system and express, at least, the transcription factor Foxp3. Tregs suppresses cytokine production and proliferation of T effector cells. Tregs do not express inflammatory cytokines such as interferon-γ, interleukin-17, and interleukin-2 and do not proliferate when stimulated via the T cell receptor in vitro.

Several methods are used to identify Tregs. For example, all Tregs express the CD4 and CD25 proteins, and thus are CD4+ and CD25+. Such proteins are therefore referred to as markers, or marker proteins, for Tregs. Thus, in one embodiment, the isolated cells comprise Tregs that are at least CD4+CD25+. Such cells make up about 5-10% of the mature CD4+ T-cell population in humans, and about 1-2% of CD4+ cells in whole blood. However, because the CD25 protein can also be expressed on non-regulatory cells during activation of the immune system, a more accurate identification of Tregs in a cell population can be made by detecting expression of the transcription factor protein, forkhead box p3 (Foxp3). Thus, in one embodiment, the isolated cells comprise Tregs that are at least CD4+CD25+Foxp3+. A small percentage of Tregs may express Foxp3, but express low to undetectable levels of CD25. Detection of the presence or absence of other marker proteins can improve this analysis even further. Such markers include, for example, Helios (a member of the Ikaros family of zinc finger proteins) and CD127. With regard to CD127, the absence or low (10) levels of expression of this protein, as compared to intermediate (int) or high (hi) levels of expression, indicates the T-cell is a Treg. Methods of determining whether the expression level of CD127 is low, intermediate, or high, are disclosed herein and are known to those skilled in the art. For example Liu W, Putnam A L, Xu-Yu Z, et al. CD127 expression inversely correlates with FoxP3 and suppressive function of human CD4+ T reg cells. J Exp Med. 2006; 203(7):1701-1711, which is incorporate herein by reference, teaches that low level-expression of CD127 is one of phenotypic feature of peripheral blood-resident Tregs in healthy donors and patients and allows one to distinguish Foxp3+ Treg from Foxp3− effector cells. Accordingly, this references teaches assays for measuring the level of expression of CD127. In various embodiments, the isolated cells comprise Tregs that have at least one characteristic selected from the group consisting of: (i) being Helios+, (ii) being CD127−; and, (iii) being CD127$^{lo}$. In one embodiment, the isolated cells comprise Tregs that are CD4+CD25+/−Foxp3+Helios+. In a further embodiment, the isolated cells comprise Tregs that are CD4+CD25+/−Foxp3+Helios+CD127−. In another embodiment, the isolated cells comprise Tregs that are CD4+CD25+/−Foxp3+Helios+CD127$^{lo}$. In addition to the markers already described, Tregs of the present invention may also express high levels of cytotoxic T-lymphocyte associated molecule-4 (CTLA-4) and glucocorticoid-induced TNF receptor (GITR).

In addition to detecting the presence, absence of expression level of various protein markers, Treg's can be identified using methylation analysis. For example, in Treg cells, a region of the foxp3 gene is demethylated. This region is referred to as the Treg-specific demethylated region (TSDR). Methods of detecting methylation or demethylation of this region are disclosed in the art. (see, for example, Polanski et al., Methylation matters: binding of Ets-1 to the demethylated Foxp3 gene contributes to the stabilization of Foxp3 expression in regulatory Tcells., J. Mol. Med. (2010) 88:1029-1040, which is hereby incorporated by reference). Thus, in one embodiment, isolated cells comprise T-cells in which the TSDR is methylated.

As used herein, the term stable with regard to T-cells refers to T-cells that maintain expression of particular markers over several generations. For example, stable Tregs maintain expression of the specific Treg markers disclosed herein, over several generations. In one embodiment, stable Tregs are those that maintain expression of CD4 and at least one marker selected from the group consisting of CD25, Foxp3, Helios, CD127−, and CD127$^{lo}$. In one embodiment, stable Tregs are those that remain CD4+CD25+Foxp3 over several generations. In one embodiment, stable Tregs are those that remain CD4+CD25+Foxp3 Helios+ over several generations. In one embodiment, stable Tregs are those that remain CD4+CD25+Foxp3 Helios+ and CD127− or CD127$^{lo}$ over several generations.

As used herein, the term generation refers to a round of replication. Thus, a cell that has divided one time has gone through one generation. If the progeny cells then divided once more, the original cells are considered to have gone through two generations of replication. The use of such terms is known by those it the art. In one embodiment, stable T-cells are those maintain expression of markers of the present invention for at least about 10 generations. In one embodiment, stable T-cells are those maintain expression of markers of the present invention for at least about 15 generations. In one embodiment, stable T-cells are those maintain expression of markers of the present invention for at least about 20 generations. In one embodiment, stable T-cells are those maintain expression of markers of the present invention for at least about 25 generations. In one embodiment, stable T-cells are those maintain expression of markers of the present invention for at least about 30 generations. With regard to the number of generations, the term about is used for convenience and means plus or minus two generations.

The stable expression of markers can also be measured in days. Thus, in various embodiments, stable T-cells are Treg's that maintain expression of markers of the present invention for at least about 10 days, at least about 15 days, at least about 20 days, at least about 25 days, or at least about 30 days. With regard to such measurement, the term about is used for convenience and means plus or minus two days.

According to the present invention, once isolated cells are obtained, they are cultured in the presence of an oligonucleotide having particular characteristics. It should be noted that isolated cells may be used directly in the culture step, or they may be further purified or concentrated prior to being cultured with an oligonucleotide. For example, Tregs present in an isolated sample of cells may be identified using molecules, such as antibodies, that bind to Treg markers, thereby allowing the identification of Tregs. The identified Tregs can then be separated and pooled, or otherwise concentrated, to increase the concentration of Tregs in the sample. Methods of concentrating cells are known to those skilled in the art and include, for example, flow cytometry and the use of columns containing molecules that bind Treg markers. In one embodiment, the concentration of Tregs is increased by incubating the isolated cells with a molecule that binds Tregs and then separating Tregs from non-Tregs by flow cytometry. In such an embodiment, the molecules that bind Treg markers may be labeled with a detectable marker such as, for example, a florescent dye of a radiolabel. Suitable detectable markers are known to those skilled in the art.

As used herein, the term oligonucleotide refers to a polymer of nucleotides (or bases). Such oligonucleotides can be synthesized (e.g., using a nucleic acid synthesizer such as, for example, an Applied Biosystems Model 380B DNA synthesizer), or it can be generated by degradation (e.g., chemical or enzymatic digestion, shearing, etc.) of a larger nucleic acid molecule. Preferred oligonucleotides are oligodeoxynucleotides (ODNs). While oligonucleotides of the present invention can be any size capable of stimulating enrichment of Tregs in a population of isolated cells, the inventors have found that, surprisingly, oligonucleotides having certain length characteristics, offer advantages over oligonucleotides that are either longer or shorter. For example, the inventors have found that oligonucleotides that are too long result in a decrease in the viability of cells exposed to such oligonucleotides. Moreover, oligonucleotides that are too short do not stimulate enrichment of Tregs in a population of isolated cells. Thus, in one embodiment, oligonucleotides of the present invention are less than about 300 nucleotides in length, preferably less than about 200 nucleotides in length, less than about 100 nucleotides in length, and preferably less than about 50 nucleotides in length. It should be noted that with regard to oligonucleotides of the present invention, the term about means plus or minus 10%. Further, oligonucleotides of the present invention should be at least 10 nucleotides in length. Thus in one embodiment, the oligonucleotide is between 11 and about 199 nucleotides in length. In one embodiment, the oligonucleotide is between about 15 and about 99 nucleotides in length. In one embodiment, the oligonucleotide is between about 15 and about 50 nucleotides in length. In one embodiment, the oligonucleotide is between about 20 and about 30 nucleotides in length. In various embodiments, the oligonucleotide is selected from the group consisting of an isolated oligonucleotide 21 nucleotides in length, an isolated oligonucleotide 22 nucleotides in length, an isolated oligonucleotide 23 nucleotides in length, an isolated oligonucleotide 24 nucleotides in length, an isolated oligonucleotide 25 nucleotides in length, an isolated oligonucleotide 26 nucleotides in length, an isolated oligonucleotide 27 nucleotides in length, an isolated oligonucleotide 28 nucleotides in length, and an isolated oligonucleotide 29 nucleotides in length. In a preferred embodiment, the oligonucleotide is 25 nucleotides in length.

Oligonucleotides of the present invention can have any sequence of nucleotides. That is, the inventors have found that, surprisingly, the ability of an oligonucleotide to stimulate enrichment of Tregs in a population of isolated cells is independent of its sequence. Thus, oligonucleotides of the present invention may or may not have a pattern. In one embodiment, the oligonucleotide consists of a random sequence of nucleotides. As used herein, a random nucleotide sequence means that the order of the nucleotides was not chosen, by a person or machine (e.g., computer) to have a specific pattern, such as, for example, a protein encoding sequence, a binding site or a repeating sequence of nucleotides. That is, at each position in the oligonucleotide, there is an equal probability that any of the four possible nucleotides (i.e., adenine, guanine, cytosine and thymidine) will be present. As noted above, while the oligonucleotide can have a random nucleotide sequence, it is not precluded from containing a pattern such as, for example, a repeating run of nucleotides, a protein encoding sequence, a endonuclease recognition site or a binding site. For example, inclusion of a binding motif within, or on the end of, an oligonucleotide may be useful in purification. Thus, in one embodiment the oligonucleotide comprises a repeating pattern. In one embodiment, the oligonucleotide comprises a site selected from the group consisting of a biding motif and a restriction endonuclease recognition site. Similarly, the oligonucleotide is not precluded from being a polymer of a single type of nucleotide.

It should also be appreciated that oligonucleotides of the present invention may be modified to improve, or confer, certain characteristics on the oligonucleotide. For example, modified oligonucleotides may be more stable or have fluorescent properties. Such modifications can be made during synthesis of the oligonucleotides or afterwards. For example, modified nucleoside triphosphates, such as α-phosphorothioates, 2'-O-methyl nucleotides, 7-Deazapurine nucleosides, or 2-aminopurine can be incorporated into the oligonucleotides during synthesis. Methods of modifying nucleic acid molecules are disclosed in Verma and Eckstein, Modified Oligonucleotides Synthesis and Strategy for Users., Annu Rev. Biochem 1998. 67:99-134, which is hereby incorporated by reference. Thus, in one embodiment the oligonucleotide is modified.

Once a suitable oligonucleotide has been obtained, it is cultured with isolated cells of the present invention. According to the present invention, culturing (or incubating) the isolated cells in the presence of the oligonucleotide simply means that the oligonucleotide and the cells are brought together such that they are able to come into contact. Simply as an example of one method of achieving the goals of the invention, the cells could be placed into a vessel such as an EPPENDORF® tube, along with the oligonucleotide. The mixture could be allowed to sit for a period of time to allow the oligonucleotide and the cells to come into contact, after which the mixture could be plated or introduced to culture bottles for growth. As an alternative example, the isolated cells and the oligonucleotide could be introduced directly into culture plates or bottles. Any such technique can be used, so long as the oligonucleotide and the isolated cells are allowed to come into contact.

Once the oligonucleotide and the cells have been mixed, they are then cultured (or incubated) to allow expansion of at least a portion of the T-cell population present in the isolated cells. Preferably, incubation results in expansion of at least a portion of the Treg cell population present in the isolated cells. As used herein, expansion of a cell population means that at least one cell within a population is able to grow and divide, resulting in a population of cells retaining the characteristics of the original (progenitor) cell(s). Thus, for example, if a culture containing a single cell is expanded for five generations, the expanded culture will contain 32 ($2^5$) cells. If the expanded cells are a stable population of cells, all 32 cells will retain the characteristics (e.g., express the same marker proteins, such as, CD4, CD25, Helios, Foxp3, etc) as the progenitor cell. General methods of culturing cells so that they grow and expand are known to those skilled in the art. Accordingly, it will be appreciated that culture conditions may vary depending on the types of cells being expanded, and/or the characteristics desired of the expanded cells. With regard to the present invention, the cells may be expanded in the presence of certain molecules that favor, or are necessary for, the expansion of T cells, and in particular Tregs. The requirement of the present method for inclusion of an oligonucleotide has already been described. In one embodiment, the isolated cells are expanded in the presence of at least one molecule selected form the group consisting of anti-CDR antibody, anti-CD28-antibody, interleukin-2 (IL-2), inhibitors of the mTOR pathway, rapamycin, functional analogs of the afore-mentioned molecules, and mixtures thereof.

Once the appropriate incubation conditions have been established, the cells and oligonucleotide are cultured so that the population of Treg cells expands, yielding a final population of cells that is enriched for regulatory T-cells. As has been previously discussed, only a small percentage of mature CD4+ T-cells in humans are Treg's. Moreover, while approximately 98% of Treg's present in blood retain their immunosuppressive function upon isolation from blood, following expansion of such cells using currently available methods, only about 15-20% of the expanded cells retain such function. However, the methods disclosed herein provide enriched populations of cells in which at least 50% or more of the cells are Tregs. As used herein, the term enriched, with respect to T-cell populations, refers to a population of cells in which at least about 50% of the cells in the expanded cell population are stable Tregs. That is, at least 50% of the T-cells in the population maintain the ability to suppress immune function. Thus, in one embodiment, at least about 50% of the T-cells in the population are stable Tregs. In one embodiment, at least about 60% of the T-cells in the population are regulatory T cells. In one embodiment, at least about 70% of the T-cells in the population are stable Tregs. In one embodiment, at least about 75% of the T-cells in the population are stable Tregs. In one embodiment, at least about 80% of the T-cells in the population are stable Tregs. In one embodiment, at least about 85% of the T-cells in the population are stable Tregs. In one embodiment, at least about 90% of the T-cells in the population are stable Tregs. In one embodiment, at least about 95% of the T-cells in the population are stable Tregs.

As has been described, upon culture of Tregs isolated from blood, a large percentage of such cells lose markers associated with Tregs. Furthermore, the inventor shave herein described how expansion of such cells in the presence of an oligonucleotide results in a culture enriched for stable Tregs. It will be appreciated by those skilled in the art that loss of Tregs during expansion of isolated cells could result from loss of expression of Treg markers, or failure of Treg cells, which by definition express such markers, to expand. Without being bound by theory, the inventors believe that the oligonucleotide exerts a direct effect on Tregs, thereby stabilizing, or maintaining, expression of Treg markers during the expansion of such cells. Accordingly one embodiment of the present invention is a method to stabilize expression of Treg markers, the method comprising isolating cells comprising initial regulatory T-cells, and incubating the isolated cells in the presence of an oligonucleotide of the present invention, under conditions that result in the expansion of at least some of the initial, regulatory T-cells. Such a method yields progeny Treg cells that stably express Treg markers. In one embodiment, the expanded Tregs stably express CD4 and at least one marker selected from the group consisting of CD25, Foxp3, Helios, and CD127$^{lo}$. In one embodiment, the expanded Tregs stably express CD4, CD25, and Foxp3. In one embodiment, the expanded Tregs stably express CD4, CD25, Foxp3 and Helios.

In one embodiment, the expanded Tregs stably express CD4, CD25, Foxp3, Helios, and CD127$^{lo}$.

It has previously been described that the concentration of Tregs in a composition of isolated cells may be increased prior to incubating the isolated cells with an oligonucleotide. Thus, it should be appreciated that concentration of Tregs may also be performed following incubation of the isolated cells with the oligonucleotide. As has been described, concentration of Tregs may be achieved by identifying Tregs using a molecule that binds Treg markers, and then concentrating the identified cells using techniques such as, for example, flow cytometry and columns containing molecules that bind to Treg markers.

Methods of the present invention result in the production of compositions having stable regulatory T-cells, which can be used for treating various disease related to the immune system. Prior to the inventors discovery, such compositions were impractical, or even impossible, to produce, due to various factors such as cost and technical difficulties such as the spontaneous instability of functional Tregs (CD4+ Foxp3+Helios+). Thus, one embodiment of the present invention is a composition comprising cells, wherein greater than about 50% of the cells are stable Tregs. One embodiment of the present invention is a composition comprising isolated T-cells, wherein at least about 60% of the T-cells are stable Tregs. In one embodiment, the stable Tregs are positive for CD4 and at least one marker selected from the group consisting of CD25, Foxp3, Helios, CD127−, and/or CD127$^{lo}$. In one embodiment, stable Tregs are CD4+CD25+ Foxp3+. In one embodiment, stable Tregs are CD4+CD25+ Foxp3 Helios+. In one embodiment, stable Tregs are CD4+ CD25+Foxp3 Helios+ and CD127− or CD127$^{lo}$. In one embodiment, the composition is produced using a method comprising isolating cells comprising initial regulatory T-cells, and incubating the isolated cells in the presence of an oligonucleotide having particular characteristics, under conditions that result in the expansion of at least some of the initial, regulatory T-cells Because Tregs are able to suppress activation of the immune system, such cells can be used to treat an individual having a disease for which suppression of the immune system is desirable. Compositions of the present invention are particularly useful for treating autoimmune diseases. For example, Tregs can be used to treat or prevent a disease or condition such diabetes, multiple sclerosis, graft vs. host disease (GVHD) (e.g., after a bone marrow transplantation), allograft rejection following tissue transplantation, and the like. Thus, one embodiment of the present invention is a method to treat an individual in need of such treatment, the method comprising administering a composition comprising isolated T-cells, wherein at least about 60% of the T-cells are stable Tregs. In one embodiment, at least about 70% of the T-cells in the composition are stable Tregs. In one embodiment, at least about 80% of the T-cells in the composition are stable Tregs. In one embodiment, at least about 90% of the T-cells in the composition are stable Tregs. In one embodiment, at least about 95% of the T-cells in the composition are stable Tregs.

The terms individual, subject, and patient are well-recognized in the art, and are herein used interchangeably to refer to a mammal, including dog, cat, rat, mouse, monkey, cow, horse, goat, sheep, pig, camel, and, most preferably, a human. In some embodiments, the subject has been diagnosed with an autoimmune disease. In some embodiments, compositions of the present invention are administered to an individual at risk for developing an autoimmune disease. Such risk can be due to, for example, genetic factors or exposure to environmental factors. Methods of identifying individuals at risk for developing an autoimmune disease are known to those in the art.

The terms individual, subject, and patient by themselves do not denote a particular age, sex, race, and the like. Thus, individuals of any age, whether male or female, are intended to be covered by the present disclosure. Likewise, the methods of the present invention can be applied to any race, including, for example, Caucasian (white), African-American (black), Native American, Native Hawaiian, Hispanic, Latino, Asian, and European.

Compositions of the present invention are administered using any known route used to administer therapeutic compositions, so long as such administration results in alleviation of symptoms of an autoimmune disease. Acceptable protocols by which to administer compositions of the present invention in an effective manner can vary according to individual dose size, number of doses, frequency of dose administration, and mode of administration. Determination of such protocols can be accomplished by those skilled in the art.

Also included in the present invention are kits useful for practicing the disclosed methods of the present invention. Thus, one embodiment of the present invention is a kit for producing a population of cells that is enriched for stable, regulatory T-cells (Tregs), the kit comprising (i) oligonucleotides of the present invention and ii) instructions for using the kit. Kits of the present invention can also comprise various reagents, such as buffers, necessary to practice the methods of the invention, as known in the art. Such reagents and buffers may, for example, be useful for establishing conditions appropriate for expanding isolated cells into enriched populations of Tregs. Thus, such regents may include things such as, for example, tissue culture media and immunoregulatory molecules such as IL-2.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The following examples are provided for the purpose of illustration and are not intended to limit the scope of the present invention.

EXAMPLE 1

The possibility that instability of Treg cell populations might be related to the different properties of the Helios$^+$ and Helios⁻ subpopulations, was explored. One epigenetic marker that has been used to distinguish nTreg from iTreg is the methylation status of the Treg specific demethylation region (TSDR) of the Foxp3 gene (Floess S, Freyer J, Siewert C, et al., *PLoS Biol*, 2007; 5(2):e38). Demethylation of the TSDR region correlates with the thymic origin of Foxp3⁺ T cells and stable expression of Foxp3, while T cells induced to express Foxp3 in vitro have a fully methylated TSDR region and lose expression of Foxp3 in vivo or in vitro.

To determine if a correlation exists between Helios expression and TSDR methylation status, four different CD4⁺ subsets (Foxp3⁺Helios⁺, Foxp3⁺Helios⁻, Foxp3⁻Helios⁺, and Foxp3⁻ Helios⁻) were isolated and expression of various proteins analyzed. Briefly, human PBMCs were obtained from 20-80 year-old healthy male donors by Department of Transfusion Medicine at National Institutes of Health. CD4⁺CD25$^{hi}$CD127⁻ Tregs were isolated by cell sorting on a FACSAria. Sorted Treg (0.2×10⁶) cells were re-suspended in complete RPMI-1640 supplemented with 10% heat-inactivated fetal calf serum, and stimulated in plates coated with anti-CDR (10 μg/ml) and anti-CD28 (2 μg/ml) in the presence of IL-2 (150 U/ml) for 5-6 days. Stimulated cells were washed in RPMI 1640-10 media twice and expanded in complete RPMI 1640-10 with recombinant IL-2 (150 U/ml) for 5-10 days in the presence of Treg-expander magnetic beads (Cell:Bead=4:1). To evaluate the purity of sorted Tregs, cells were stained with anti-Foxp3 and anti-Helios (Biolegend) in Foxp3-staining buffer (eBioscience). All flow cytometry was performed on a FACS LSRII flow cytometer (Becton Dickinson) and analyzed with FlowJo software (TreeStar).

To determine the methylation status of the TSDR, freshly isolated, or in vitro expanded, Tregs were harvested, and washed twice in PBS. Extraction of genomic DNA was performed using the DNeasy Blood & Tissue Kit (Qiagen). Fixed, stained cells were FACS sorted, washed in PBS twice, and genomic DNA was extracted with QIAamp DNA FFPE tissue Kit (Qiagen). Bisulfite conversion, pyrosequencing, and data analysis were done by EpigenDx (Worcester, Mass.). 11 CpGs of the human TSDR were analyzed (−2376 to −2263 from TSS, ENST00000376207). The percent methylation of each sample indicates the mean value of all 11 CpGs.

The results of this analysis are shown in FIG. 1A. Foxp3⁻ T cells expressed a fully methylated TSDR regardless of Helios expression. In contrast, Foxp3⁺Helios⁺ cells were fully demethylated in all donors, while the TSDR region of the Fox3⁺Helios⁻ subset was ~45% methylated. One interpretation of these results is that the Foxp3⁺Helios⁻ subpopulation is composed of two subpopulations, one of which expresses a fully methylated TSDR that can potentially lose Foxp3 expression upon in vitro expansion, while the second likely represents a population with greater stability of Foxp3 expression. These results demonstrate that CD4+Foxp3+ Helios+ Tregs are stable, and possess a demethylated TSDR.

EXAMPLE 2

Previous work had shown that a low percentage (1-5%) of freshly explanted Foxp3⁺ T cells produce effector cytokines (IL-2, IFNγ), and that almost all the cytokine producing cells were in the Foxp3⁺Helios⁻ subpopulation (Liu H, Komai-Koma M, Xu D, Liew F Y, *Proc Natl Acad Sci USA*, 2006; 103(18):7048-7053). Thus, the ability of cell populations that were expanded using the presently disclosed methods was measured.

CD4⁺CD25⁺ T cells were isolated and sorted as described in Example 1, and expanded for 12 days by stimulation with plate-bound anti-CD3 and anti-CD28 in the presence of IL-2. While ~90% (data not shown) of the starting population was Foxp3⁺, after 12 days of expansion only 45% of the cells remained Foxp3⁺ (FIG. 1B). Upon re-stimulation in vitro with phorbol myristate acetate (PMA)/ionomyin, 20% of the expanded Foxp3⁺Helios⁻ subpopulation produced IL-2 or IFNγ, while the frequency of cytokine producers remained low in the Foxp3⁺Helios⁺ subpopulation (FIG. 1B). These results suggest that one factor controlling the maintenance of Foxp3 expressing Tregs upon expansion in vitro is the heterogeneity of the starting population. The Foxp3⁺Helios⁻ subpopulation appears to contain a high percentage of Tregs with methylated TSDRs that have the potential for loss of expression of Foxp3. This same subpopulation also contains a high percentage of effector cytokine producing cells that would not be ideal for cellular immunotherapy.

EXAMPLE 3

This Example demonstrates that addition of CpG ODN to cell cultures results in enhanced maintenance of Foxp3+ Helios+ cells during in vitro expansion.

Figure 2:
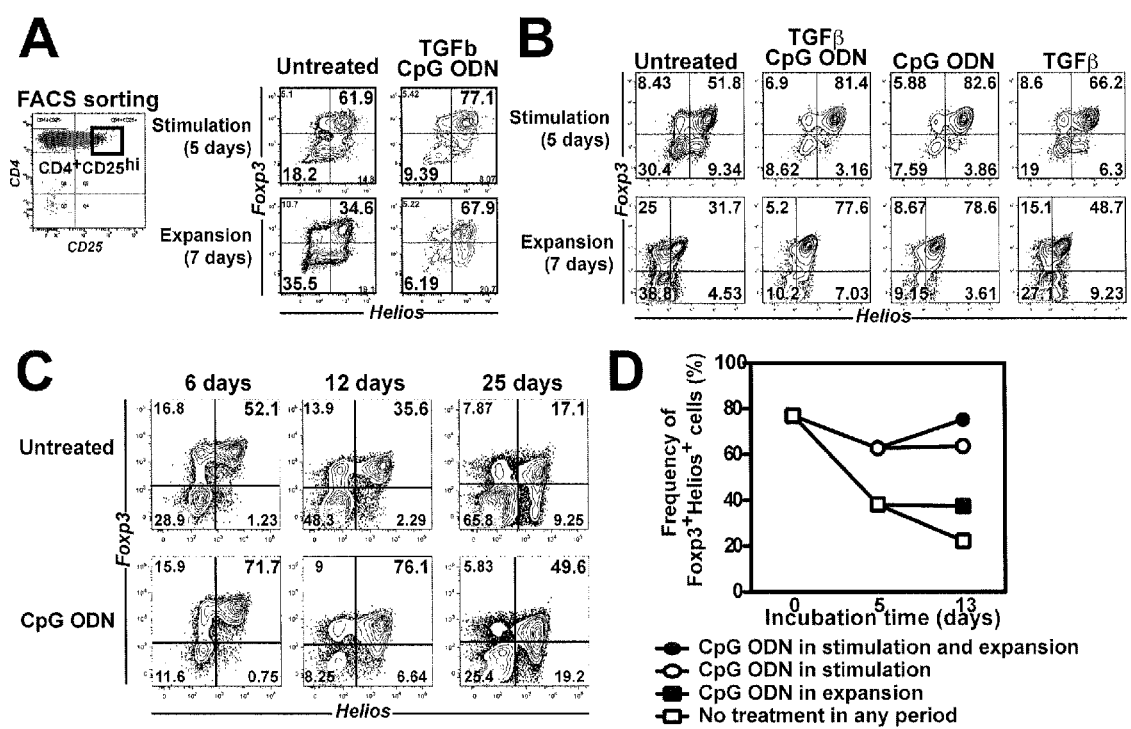
FIG. 2. Addition of CpG ODN Increases the Frequency of Foxp3$^+$Helios$^+$ Cells During In Vitro Expansion. (A) FACS-sorted CD4$^+$CD25$^+$ cells (square gate in left plot) were stimulated with plate-bound anti-CD3 and anti-CD28 in the presence of TGFβ (5 ng/ml) and CpG ODN (ODN2395, 2.5 μM) for 5 days. The cells were then washed and incubated for two additional days in IL-2 containing media. Foxp3 and Helios staining was performed on gated viable CD4$^+$ cells. (B) Flow cytometry data showing that CpG ODN, not TGFβ, mediates the enhancement of the frequency of Foxp3$^+$Helios$^+$ cells. (C) Flow cytometry data showing that the CpG ODN induced frequency of Foxp3$^+$Helios$^+$ cells is maintained during prolong expansion cultures. Cells were sorted as in (A), stimulated for 5 days with plate-bound anti-CD3/CD28, washed, and then expanded for the indicated periods of time with anti-CD3/CD28 beads and IL-2. (D) Graph showing that CpG ODN enhances the frequency of Foxp3$^+$Helios$^+$ cells in both freshly isolated and pre-activated T cells. Cells were isolated and stimulated for 5 days as in (A). The CpG ODN was added at the time points indicated in the figure.

Initially, two potential candidates were selected for testing: TGFβ, and the toll-like receptor 9 (TLR9) agonist CpG oligodeoxynucleotide (ODN). CD4⁺CD25⁺ cells, sorted as described in Example 1, were stimulated with plate-bound anti-CD3 and anti-CD28 in the presence of TGFβ (5 ng/ml) or CpG ODN (ODN2395, 2.5 μM) for 5 days. The cells were then washed and incubated for two additional days in IL-2 containing media. Foxp3 and Helios staining was performed on gated viable CD4⁺ cells. The results of this analysis, which are shown in FIG. 2, show that the frequency of the Foxp3⁺Helios⁺ positive cells was higher in cells expanded in the presence of TGFβ and the ODN as compared to cells expanded in the absence of TGFβ and the ODN (FIG. 2A). The 5 day expanded cells were then washed, and re-stimulated for an additional 7 days in the absence of TGFβ and CpG ODN. The results of this analysis, which are shown in FIG. 2B, show that cells initially exposed to TGFβ/ODN maintained a higher frequency (67.9%) of Foxp3⁺Helios⁺ cells, while cells initially expanded in the absence of TGFβ/ODN had a markedly decreased percentage (34.6%) of the Foxp3⁺Helios⁺ cells. The results further indicate that CpG ODN was the major factor involved in stabilization of the Foxp3⁺Helios⁺ population, since cells expanded in the presence of TGFβ alone had only a modest increase in Foxp3⁺ Helios⁺cells, while cells expanded with the ODN alone resembled the population treated with the combination of TGFβ/ODN (FIG. 2B).

To determine the longevity of the effects of the ODN on maintenance of the Foxp3⁺Helios⁺cells, FAC-sorted CD4⁺ CD25$^{hi}$ cells were expanded in the presence or absence of the ODN for 5 days, washed, and expanded for an additional 6 or 19 days in the presence of anti-CD3/CD28 beads and IL-2. These results are shown in FIGS. 2C and 2D. Marked enhancement of the frequency of the Foxp3⁺Helios⁺cells was observed after 12 days in culture and the enhancement was still prominent after a total of 25 days in culture even though some decrease in the frequency of the Foxp3⁺Helios⁺ cells was observed in the cells initially exposed to the ODN (FIG. 2C). It was observed that the continuous presence of the ODN for the entire 12 days of expansion resulted in a modest increase (75.3% vs 63.7%) in the frequency of Foxp3⁺Helios⁺cells compared to cells that had just been treated for the initial 5 days (FIG. 2D). Interestingly, when cells that had been previously expanded for 5 days in the absence of the ODN, were re-stimulated for 7 additional days in the presence of the ODN, stabilization (38.1% vs 22.2%) of the frequency of Foxp3$^+$Helios$^+$ cells was observed (FIG. 2D). Thus, the ODN exerts a stabilizing effect on Foxp3$^+$Helios$^+$ cells that had been previously stimulated in the absence of the ODN.

EXAMPLE 4

This Example demonstrates that Foxp3$^+$Helios$^+$ cells expanded with CpG ODN are functional Tregs.

Figure 1:
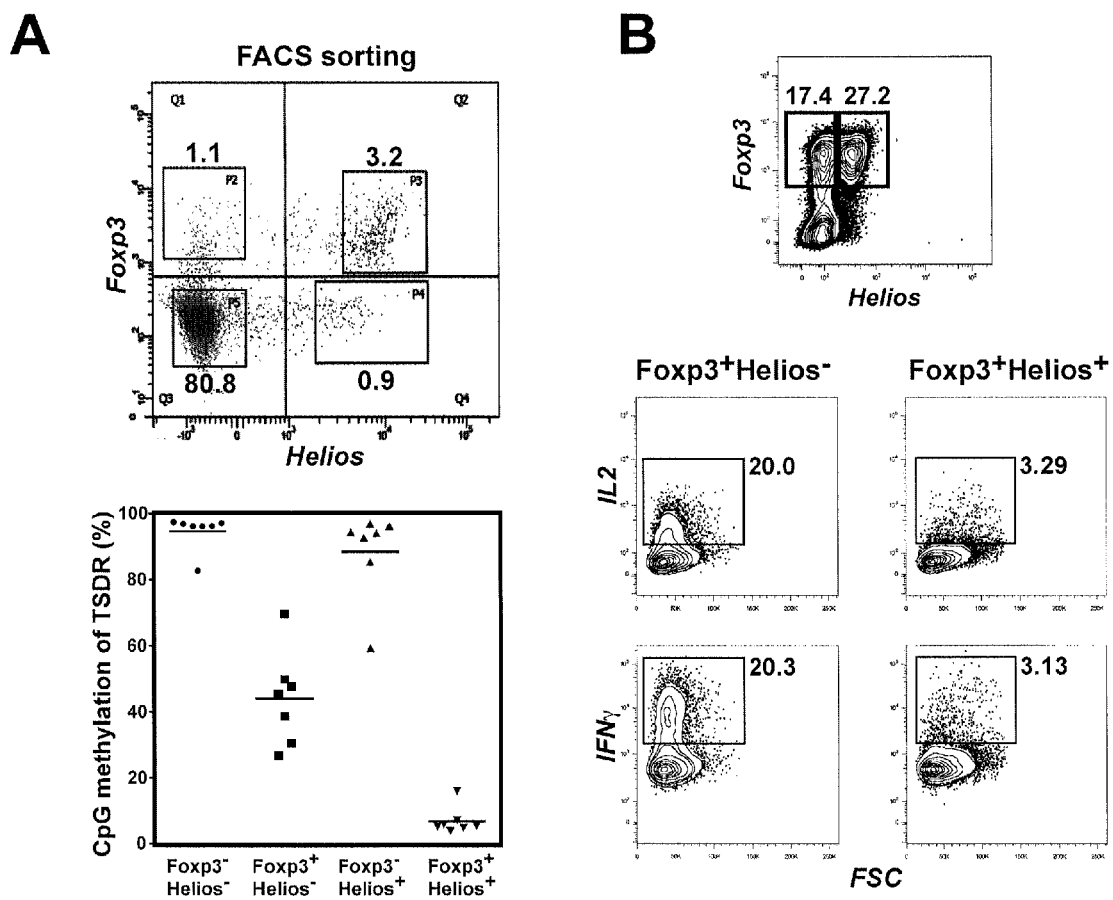
FIG. 1. Foxp3$^+$Helios$^+$ Tregs have Uniformly Demethylated TSDR and do not Produce Inflammatory Cytokines. (A) Cells were isolated from the buffy coat of a male donor, fixed-permeabilized, and stained for intracellular expression of Foxp3 and Helios. Stained cells were sorted into the 4 different fractions. Upper plot shows the staining and gating condition before sorting. For DNA methylation analysis of the TSDR, bisulfite modification of genomic DNA was performed after extraction from the sorted fractions. Methylation of CpG was read and analyzed by the pyrosequencing method. Results from 7 donors are shown in the lower plot. (B) CD4$^+$CD25$^+$ cells were sorted from the buffy coat and were stimulated with plate-bound anti-CD3 and anti-CD28 antibodies for 5 days. The cells were the expanded for an additional 5 days with anti-CD3/anti-CD28 antibody-coated magnetic beads (CD3/CD28-beads). Intracellular staining for cytokine production was performed after restimulation with PMA and ionomycin. Data shown is one of three independent experiments.
Figure 3:
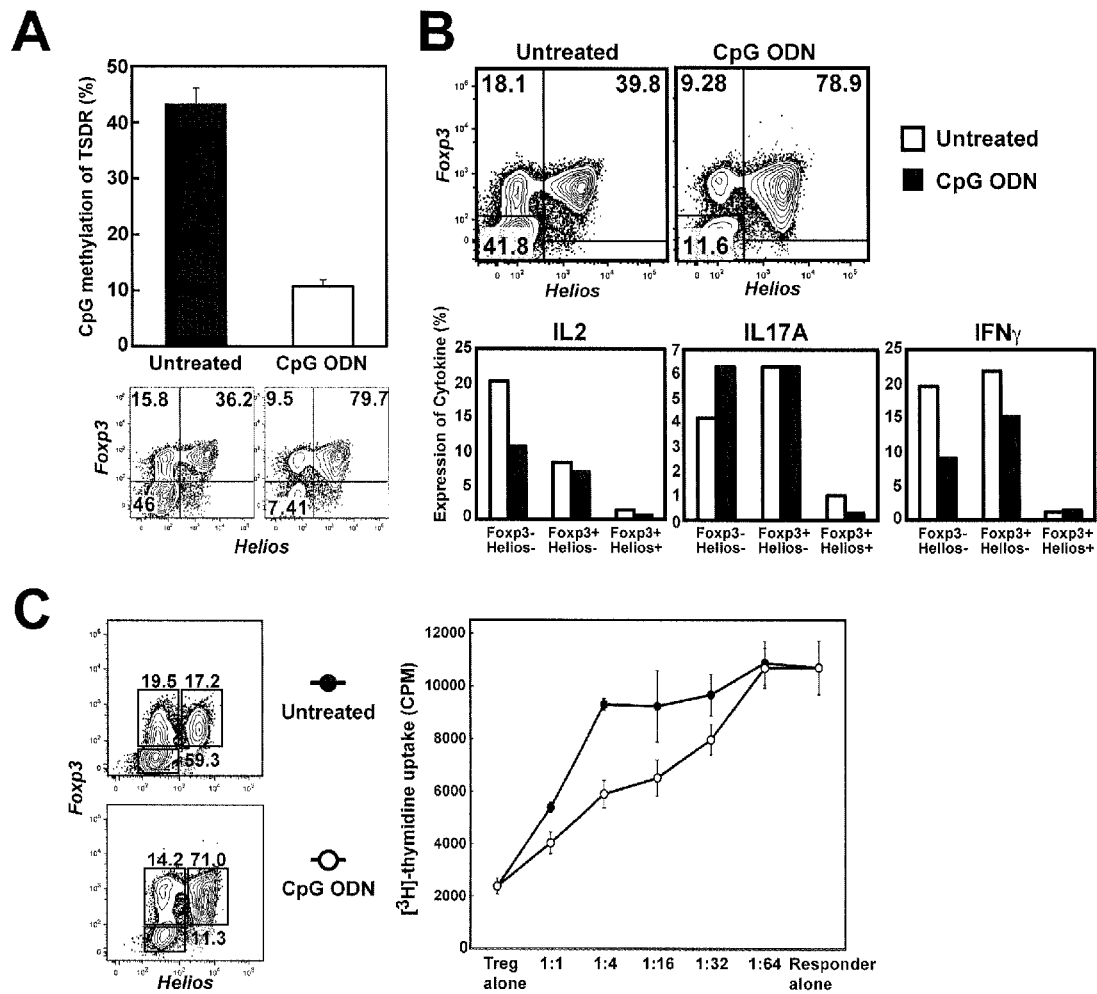
FIG. 3. The Foxp3$^+$Helios$^+$ T Cells Expanded in the Presence of the CpG ODN are Functional Tregs. (A) The TSDR of CD4$^+$CD25$^+$ T cells expanded in the presence of the CpG ODN is fully demethylated. Same protocol as in FIG. 1a except that cells are expanded for 9 days. (B) The 9 day expanded cells were treated as in FIG. 1b with PMA/ionomycin and analyzed for intracellular cytokines expression. (C) The population of cells expanded in the presence of the CpG ODN exhibits greater suppressive activity than cells expanded in the absence of the ODN. Tregs were expanded as in (A) and cultured for three days at different ratios with freshly isolated CD4$^+$CD25$^-$ cells (5×10$^4$ cells/well) in the presence of γ-irradiated PBMCs (5×10$^4$) and soluble anti-CD3 (2 μg/ml). $^3$H-TdR incorporation was measured during the last 18 hours of culture.
Figure 8:
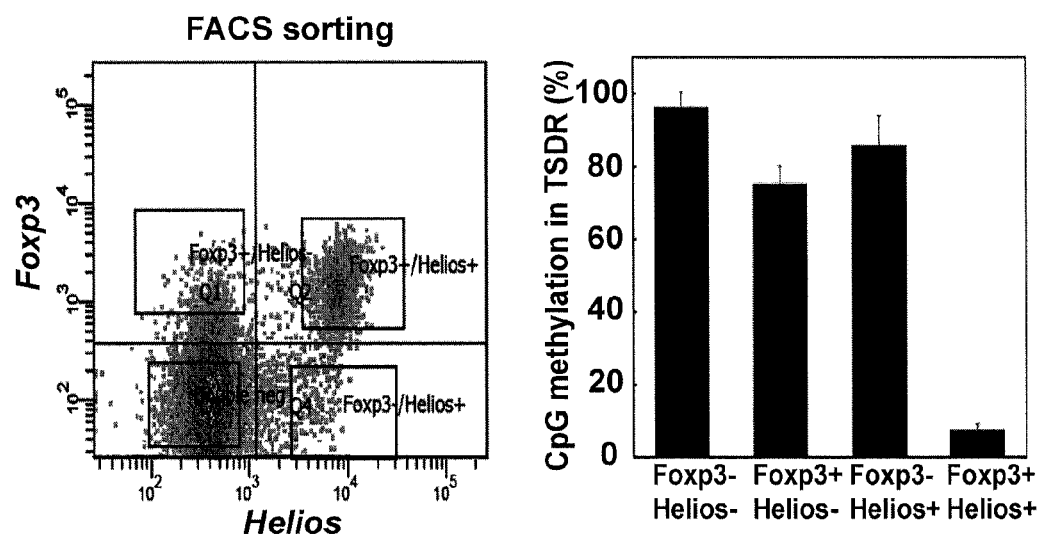
FIG. 8. Methylation Status of the TSDR in Expanded Treg Subpopulations.

Foxp3$^+$ Treg cells were expanded in vitro for 25 days and the methylation status of the TSDR analyzed, as described in Example 1. The results, which are shown in FIG. 1 and FIG. 8, show that expanded Foxp3$^+$Helios$^+$ cells expressed a fully demethylated TSDR, while the TSDR of the expanded Foxp3$^+$Helios$^-$ cells was 70% methylated, a value higher than that observed with freshly isolated Foxp3$^+$Helios$^-$ cells. Next, TSDR methylation in Foxp3$^+$ cells expanded in the presence or absence of the ODN for 25 days was compared. The results, which are shown in FIG. 3, show that CpG ODN treatment resulted in a high frequency of Foxp3$^+$Helios$^+$ cells (79.7% vs 36%). The TSDR of the entire population of cells expanded in the presence of the CpG ODN was almost completely (90%) demethylated, while the TSDR of the cells expanded in the absence of the ODN was 42% methylated.

To determine the effect of long-term expansion on the ability of cells to produce cytokines, cell populations that had been expanded for 25 days in the presence or absence of the ODN were re-stimulated for 4 hours with PMA/ionomycin, and cytokine production by gated Foxp3$^+$Helios$^+$ and Foxp3$^+$Helios$^-$ populations was measured. The results, which are shown in FIGS. 3B and 3c, show that Foxp3$^+$Helios$^+$ Tregs expanded in the presence of the ODN produced low to undetectable levels of IL-2, IFNγ, or IL-17, while Foxp3$^+$Helios$^-$ cells produced significant levels of all three cytokines. In addition, the population of Foxp3$^+$ T cells that had been expanded in the presence of the ODN, which contained a high percentage of Foxp3$^+$Helios$^+$ T cells, exhibited greater suppressive activity in a standard in vitro suppression assay (FIG. 3C) than cells that had been expanded in the absence of the ODN. Taken together, these studies demonstrate that the Foxp3$^+$Helios$^+$ cells that had been expanded in the presence of the ODN retain all the properties of fully functional Tregs.

EXAMPLE 5

This example demonstrates the ability of CpG ODN to stabilize Foxp3 and Helios expression in all Treg subsets.

Figure 4:
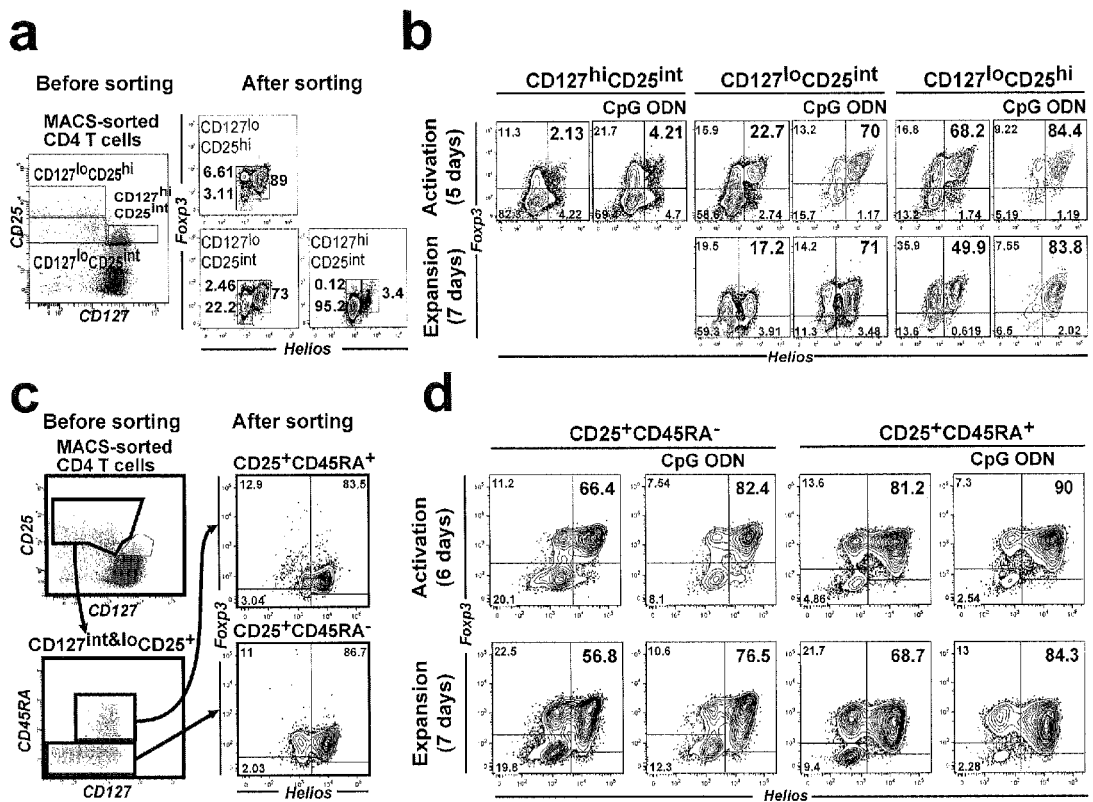
FIG. 4. An Increased Frequency of Foxp3$^+$Helios$^+$ T Cells is Seen in the Presence of the CpG ODN During Expansion of Distinct Populations of Tregs. (A) Sorting strategy used for isolation of CD127$^{hi}$CD25$^+$, CD127$^{lo}$CD25$^{int}$, and CD127$^{lo}$25$^{hi}$ T cells. Expression of Foxp3 and Helios was analyzed in the different populations after sorting. (B) CpG ODN-mediated enhancement of the frequency of Foxp3$^+$Helios$^+$ cells in the sorted populations. (C) Sorting strategy for the isolation of CD25$^+$CD45RA$^+$ and CD25$^+$CD45RA$^-$ Treg subpopulations. Expression of Foxp3 and Helios in the cells was performed after sorting. (D) CpG ODN-mediated enhancement of the frequency of Foxp3$^+$Helios$^+$ cells in the sorted CD25$^+$CD45RA$^+$ and CD25$^+$CD45RA$^-$ Treg subpopulations.

Co-expression of CD25 and low levels of CD127 has been used to distinguish CD25$^+$Foxp3$^+$ from CD25$^+$Foxp3$^-$ Teff cells (Hippen K L, Merkel S C, Schirm D K, et al., *American Journal of Transplantation*, 2011; 11(6):1148-1157). In order to determine the relationship between Foxp3/Helios expression and the level of expression of CD127, freshly isolated CD4$^+$ T cells were sorted into three different subsets based on expression of CD25 and CD127, and the relative expression of Foxp3 and Helios analyzed. The results, which are shown in FIG. 4A, show that most CD127$^{hi}$CD25$^{int}$ cells did not express either Foxp3 or Helios. However, both CD127$^{low}$ CD25$^{hi}$ and CD127$^{low}$CD25$^{int}$ contained a high percentage of Foxp3$^+$Helios$^+$ T cells. To further explore the relationship between these markers, these three subpopulations (CD127$^{low}$CD25$^{hi}$, CD127$^{low}$ CD25$^{int}$ and CD127$^{hi}$CD25$^{int}$ T cells) were sorted and expanded in the presence or absence of the CpG ODN. The results, which are shown in FIG. 4B, show that ODN had minimal effects on the composition of the CD127$^{hi}$CD25" cells except for a slight increase in the Foxp3$^+$Helios$^-$ subset (11.3% to 21.7%, left two panels in FIG. 4B). Addition of the ODN to the expansion of CD127$^{hi}$CD25$^{int}$ cells enhanced the recovery of Foxp3$^+$ Helios$^+$ cells (68.2% vs 89%) on day 5 and this enhancement was maintained for an additional 7 days of culture in the absence of the ODN. The most interesting results were observed with the CD127$^{low}$ CD25$^{int}$ cells which rapidly lost Foxp3$^+$Helios$^+$ cells (73% to 22.7%) during the initial 5 days of expansion, but retained Foxp3$^+$Helios$^+$ cells when expanded in the presence of the ODN (73% to 71%) and maintained this frequency of Foxp3$^+$Helios$^+$ cells after a further 7 days expansion in the absence of the ODN. These results suggest that the subpopulation of Foxp3$^+$Helios$^+$ cells that express lower levels of CD25 are much less stable than those that express higher levels of CD25, but that expansion in the presence of the ODN exerts a major effect on Foxp3/Helios stabilization in this subpopulation.

In addition to the use of the levels of CD127 expression to isolate Foxp3$^+$ Treg cells, co-expression of CD25 and CD45RA has defined a subpopulation of Foxp3$^+$ T cells that are regarded as naïve[11], exhibit more stable Foxp3 expression on expansion in vitro[17], and express fully demethylated TSDRs (Hoffmann P, Boeld T J, Eder R, et al., *Eur J Immunol*, 2009; 39(4):1088-1097). Thus, a comparison of Helios expression in Foxp3$^+$ CD45RA$^+$ and Foxp3$^+$ CD45RA$^-$ cells revealed that the frequency of Foxp3$^+$ Helios$^+$ cells was similar in these two subpopulations (data not shown). To further explore this area, CD45RA$^+$ and CD45RA$^-$ cells were sorted from CD4$^+$CD25$^+$CD127$^{low}$ peripheral CD4$^+$ T cells (FIG. 4C), and all three groups stimulated in the presence or absence of CpG ODN for 6 days, washed, and expanded in the absence of the ODN for an additional 6 days. The results, which are shown in FIG. 4D, show that after 6 days of stimulation without ODN, 94% of CD25$^+$CD45RA$^+$ cells remained Foxp3+, whereas CD25$^+$CD45RA$^-$ subpopulation began to lose Foxp3 expression (98% to 77.6%). The frequency of Foxp3$^+$Helios$^+$ cells was also somewhat higher in the CD25$^+$ CD45RA$^+$ subpopulation (81%) than in CD25$^+$CD45RA$^-$ group (66%). Both cell populations had decreased frequencies of Foxp3$^+$Helios$^+$ T cells after an additional 6 days of expansion in the absence of the ODN, although the total frequency of Foxp3$^+$ cells remained stable. Addition of the ODN to both groups resulted in enhanced frequencies of Foxp3$^+$Helios$^+$ cells during the second 6 days of expansion in the absence of the ODN. Thus, Foxp3$^+$ CD45RA$^+$ cells appear to exhibit more stable expression of Foxp3 upon expansion in vitro, but the frequency of Foxp3$^+$Helios$^+$ cells does diminish and can be rescued in both the CD45RA$^+$ and CD45RA$^-$ populations by stimulation in the presence of the ODN.

EXAMPLE 6

This example demonstrates that CpG ODN directly stabilize Helios-expressing Foxp3$^+$ cells and do not inhibit the proliferation of Foxp$^+$Helios$^-$ or Foxp3$^-$Helios$^-$ cells.

Figure 5:
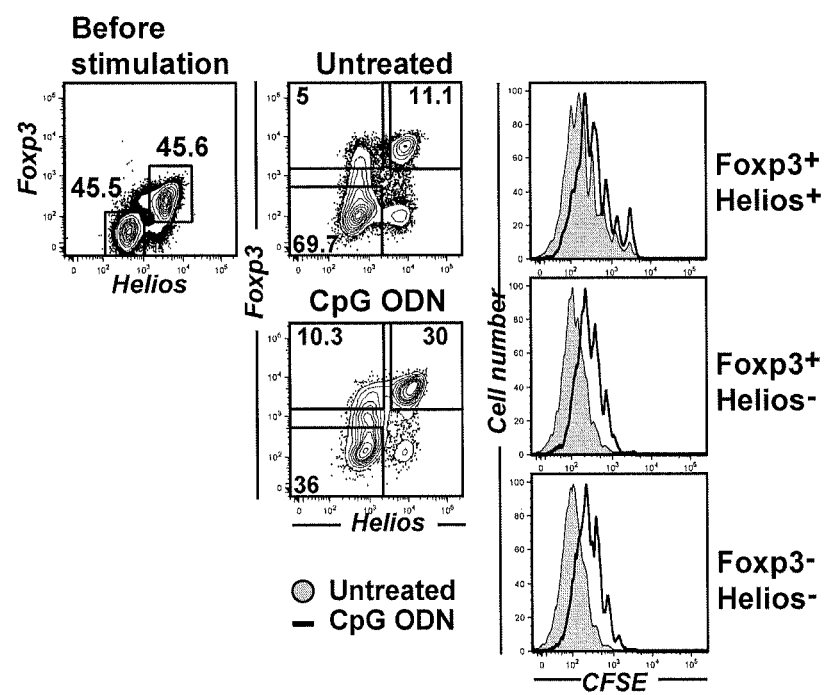
FIG. 5. CpG ODN Acts Directly on Foxp$^+$Helios$^+$Cells. The enhancement of the frequency of Foxp3$^+$Helios$^+$ Tregs by CpG ODN is not secondary to differential effects of the ODN on the proliferation of Foxp3$^+$Helios$^+$, Foxp3$^+$Helios$^-$, or Foxp3$^-$Helios$^-$ subpopulations. A mixture containing 50% CD4$^+$CD25$^+$ and 50% CD4$^+$CD25$^-$ T cells was created after sorting. Following labeling with CFSE, the mixture was stimulated with plate-bound anti-CD3/CD28 in the presence or absence of the CpG ODN (2.5 μM). The extent of CFSE dilution was analyzed by gating on the three subsets (Foxp3$^+$Helios$^+$, Foxp3$^+$Helios$^-$, and Foxp3$^-$Helios$^-$).

To investigate whether CpG ODN affect cell populations through a direct effect on existing Foxp3$^+$ Helios$^+$ cells or a suppressive effect on the expansion of Foxp3$^+$ Helios$^-$ or Foxp3$^-$ Helios$^-$ cells that are also present in the starting populations, a starting population containing 50% Foxp3+ Helios+ cells, rather than the higher percentages used in the other studies, was prepared. Such a population of cells allows observation of the differential effects of the ODN on Helios+ and Helios− cells. The mixture was labeled with carboxyfluorescein diacetate succinimidyl ester (CFSE) and the cells stimulated for 6 days in the presence or absence of the ODN. The results, which are shown in FIG. 5, show that stabilization of the Foxp3+Helios+ cells was seen after expansion in the presence of the ODN (FIG. 5, 30% vs. 11.1%). Addition of the CpG ODN slightly suppressed the proliferation of all three subsets (Foxp3+Helios+, Foxp3+ Helios−, and Foxp3−Helios−) (FIG. 5, histograms on right side). Since there was no significant difference in proliferation between the groups, the results indicate that enhanced frequency of the Foxp3+Helios+ subset in the ODN treated group is consistent with a direct stabilizing effect of the ODN on this subpopulation.

EXAMPLE 6

This example demonstrates that ODN stabilizes Helios-expressing Foxp3+ cells via a cytosolic universal DNA sensor, not via an endosomal TLR.

Figure 7:
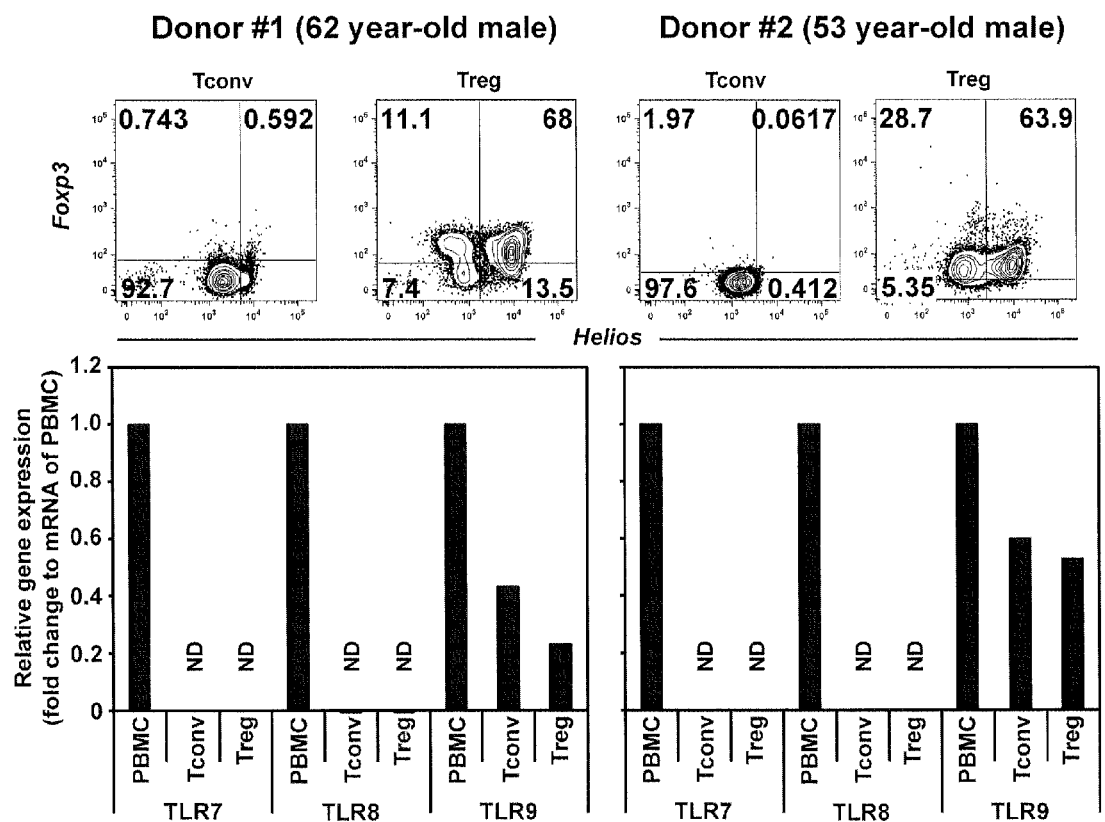
FIG. 7. Quantitative RT-PCR Analysis of Endosomal TLR's. Conventional T cells (Tconv, CD4$^+$CD25$^-$CD127$^+$) and Treg (CD4$^+$CD25$^+$CD12T$^-$) were isolated from buffy coats by FACS sorting. The purity of the isolated populations was verified by analysis of Foxp3 and Helios expression (Top plots). Extraction of total RNA was done using TRIZOL. Expression of TLR7, TLR8, and TLR9 were determined by quantitative RT-PCR. For normalization of variation between sample tubes, 18s rRNA was amplified as internal gene control.

To determine if the CpG ODN used in our studies mediates its effects on stabilization of Foxp3+Helios+ T cells by acting via TLR9, which is expressed in Foxp3+ human Tregs (FIG. 7), Tregs were expanded in the presence of both the TLR9 agonist and a TKR9 antagonist (ODN TTAGGG). Surprisingly, expansion of Tregs in the presence of both the TLR9 agonist and a TLR9 antagonist (ODN TTAGGG) resulted in stabilization of the Foxp3+Helios+ subset (FIG. 6A). When both the CpG ODN and the TLR9 antagonist were simultaneously added to the expansion cultures, reversal of the stabilization of the Foxp3+Helios+ subset was not observed (data are not shown). Although TLR8 or TLR7 expression was not detected in Tregs (by RT-PCR), the effects of a TLR8 agonist (ssRNA40) and a TLR7 agonist (CL264) were compared with the effect of a TLR9 agonist. Neither the TLR8 nor the TLR7 agonists had any effect on the stabilization of Foxp3+Helios+ T cells, while the CpG ODN enhanced the frequency of this subset as noted in our other studies (FIG. 6B). Thus, these results indicate that CpG ODN-mediated stabilization of Foxp3+Helios+ cells is mediated by TLR signaling pathway and that another nucleotide-recognizing sensor is involved in this stabilization.

To determine the optimal order, or motif, of the ODN sequence needed to stabilize Foxp3+Helios+ Treg, the TTA sequence from ODN TTAGGG was substituted with randomly selected nucleotides (NNN) and the mutants tested for their effect on the stability of Tregs. The results, which are shown in FIG. 6C, show that ODN NNNGGG behaved in identical fashion to ODN TTAGGG. Moreover, a completely randomized ODN (ODN NNNNNN) also efficiently stabilized Foxp3+Helios+ cells. As the ODN appears to be sensed in a non-sequence-specific manner, the role of the nucleotide composition on the stabilizing activity of the ODN was examined. Excluding A, T, G, or C from the random synthesized ODN did not diminish the stabilizing effect (FIG. 6D, bottom panels). In contrast to phosphorothioate ODN (ODNps), phosphodiester ODN (ODNp) failed to stabilize Foxp3+Helios+ Tregs even when the ODNp was added every 24 hours during the 5-day expansion culture (FIG. 6D, top panels, and data not shown).

EXAMPLE 7

To determine the optimal size ODN for stabilizing Foxp3+ Helios+ cells, the cell-stabilizing activity of ODNs ranging from 10mer to 100mer was measured. The results, illustrated in FIG. 6E, show that the 10mer had no activity when compared to the untreated cells, while the 50mer and 100mer increased the frequency of the Foxp3+Helios+ cells after 5 days of culture, but were also moderately toxic as their use resulted in a decreased cell yield (FIG. 10). Optimal results were obtained in the 25mer ODN-treated group including stabilization of the frequency of Foxp3+Helios+ cells and an increase in the absolute number of recovered Foxp3+Helios+ cells after 12 days of expansion.

EXAMPLE 8

To determine cellular localization of the ODN sensor, a 5'-biotin-conjugated ODN (Biotin-ODN) was synthesized and its location within the cell was determined. As shown in FIG. 6D, the biotin-labeled ODN was as active the ODNps in stabilizing expression of Foxp3+Helios+ T cells. Purified CD4+ T cells were stimulated in the presence of Biotin-ODN for 18 hours, and then evaluated for intracellular and extracellular expression of the ODN by using two different fluorescence-conjugated streptavidins (FIG. 6F, left side). In some of cells, biotin-ODN was detected on the extracellular membrane, but all of the cells possessed Biotin-ODN intracellularly. The staining pattern of Biotin-ODN was identical in Foxp3−Helios− and Foxp3+Helios+ subsets. On analysis by confocal microscopy, Biotin-ODN was not detected in the nucleus or associated with the nuclear membrane. All the ODN was aggregated in granule-like organelles in the cytoplasm (FIG. 6F). Time-course analysis of Biotin-ODN on the FACS indicated that the ODN rapidly disappeared after washing during the expansion phase in the absence of extracellular ODN (FIG. 11).

REFERENCES

1. Shevach E M. Mechanisms of foxp3+ T regulatory cell-mediated suppression. *Immunity.* 2009; 30(5):636-645.
2. Roncarolo M-G, Battaglia M. Regulatory T-cell immunotherapy for tolerance to self antigens and alloantigens in humans. *Nat Rev Immunol.* 2007; 7(8):585-598.
3. Riley J L, June C H, Blazar B R. Human T regulatory cell therapy: take a billion or so and call me in the morning. *Immunity.* 2009; 30(5):656-665.
4. Hoffmann P, Ermann J, Edinger M, Fathman C G, Strober S. Donor-type CD4(+)CD25(+) regulatory T cells suppress lethal acute graft-versus-host disease after allogeneic bone marrow transplantation. *J Exp Med.* 2002; 196(3):389-399.
5. Brunstein C G, Miller J S, Cao Q, et al. Infusion of ex vivo expanded T regulatory cells in adults transplanted with umbilical cord blood: safety profile and detection kinetics. *Blood.* 2011; 117(3):1061-1070.
6. Trzonkowski P, Bieniaszewska M, Juścińska J, et al. First-in-man clinical results of the treatment of patients with graft versus host disease with human ex vivo expanded CD4+CD25+CD127− T regulatory cells. *Clin Immunol.* 2009; 133(1):22-26.
7. Di Ianni M, Falzetti F, Carotti A, et al. Tregs prevent GVHD and promote immune reconstitution in HLA-haploidentical transplantation. *Blood.* 2011; 117(14): 3921-3928.
8. Shevach E M, Tran D Q, Davidson T S, Andersson J. The critical contribution of TGF-beta to the induction of Foxp3 expression and regulatory T cell function. *Eur J. Immunol.* 2008; 38(4):915-917.

9. Liu W, Putnam A L, Xu-Yu Z, et al. CD127 expression inversely correlates with FoxP3 and suppressive function of human CD4+ T reg cells. *J Exp Med.* 2006; 203(7): 1701-1711.
10. Hippen K L, Merkel S C, Schirm D K, et al. Generation and Large-Scale Expansion of Human Inducible Regulatory T Cells That Suppress Graft-Versus-Host Disease. *American Journal of Transplantation.* 2011; 11(6):1148-1157.
11. Miyara M, Yoshioka Y, Kitoh A, et al. Functional Delineation and Differentiation Dynamics of Human CD4+ T Cells Expressing the FoxP3 Transcription Factor. *Immunity.* 2009; 30(6):899-911.
12. Thornton A M, Korty P E, Tran D Q, et al. Expression of Helios, an Ikaros transcription factor family member, differentiates thymic-derived from peripherally induced Foxp3+ T regulatory cells. *J. Immunol.* 2010; 184(7): 3433-3441.
13. Floess S, Freyer J, Siewert C, et al. Epigenetic control of the foxp3 locus in regulatory T cells. *PLoS Biol.* 2007; 5(2):e38.
14. Liu H, Komai-Koma M, Xu D, Liew F Y. Toll-like receptor 2 signaling modulates the functions of CD4+ CD25+ regulatory T cells. *Proc Natl Acad Sci USA.* 2006; 103(18):7048-7053.
15. Chen Q, Kim Y C C, Laurence A, Punkosdy G A, Shevach E M. IL-2 controls the stability of Foxp3 expression in TGF-beta-induced Foxp3+ T cells in vivo. *J Immunol.* 2011; 186(11):6329-6337.
16. Peng G, Guo Z, Kiniwa Y, et al. Toll-like receptor 8-mediated reversal of CD4+ regulatory T cell function. *Science.* 2005; 309(5739):1380-1384.
17. Hoffmann P, Eder R, Boeld T J, et al. Only the CD45RA+ subpopulation of CD4+CD25high T cells gives rise to homogeneous regulatory T-cell lines upon in vitro expansion. *Blood.* 2006; 108(13):4260-4267.
18. Hoffmann P, Boeld T J, Eder R, et al. Loss of FOXP3 expression in natural human CD4+CD25+ regulatory T cells upon repetitive in vitro stimulation. *Eur J Immunol.* 2009; 39(4): 1088-1097.
19. Peters J H, Preijers F W, Woestenenk R, et al. Clinical grade Treg: GMP isolation, improvement of purity by CD127 Depletion, Treg expansion, and Treg cryopreservation. *PLoS ONE.* 2008; 3(9):e3161.
20. Hippen K L, Merkel S C, Schirm D K, et al. Massive ex Vivo Expansion of Human Natural Regulatory T Cells (Tregs) with Minimal Loss of in Vivo Functional Activity. *Science Translational Medicine.* 2011; 3(83): 83ra41-83ra41.
21. McClymont S A, Putnam A L, Lee M R, et al. Plasticity of human regulatory T cells in healthy subjects and patients with type 1 diabetes. *J. Immunol.* 2011; 186(7): 3918-3926.
22. Golovina T N, Mikheeva T, Brusko T M, et al. Retinoic Acid and Rapamycin Differentially Affect and Synergistically Promote the Ex Vivo Expansion of Natural Human T Regulatory Cells. *PLoS ONE.* 2011; 6(1): e15868.
23. Beltinger C, Saragovi H U, Smith R M, et al. Binding, uptake, and intracellular trafficking of phosphorothioate-modified oligodeoxynucleotides. *J Clin Invest.* 1995; 95(4):1814-1823.
24. Ewald S E, Lee B L, Lau L, et al. The ectodomain of Toll-like receptor 9 is cleaved to generate a functional receptor. *Nature.* 2008; 456(7222):658-662.

What is claimed:

1. A method for producing a population of cells having stable, regulatory T cells, the method comprising culturing an initial population of regulatory-T-cells in the presence of interleukin-2, an anti-CD3 antibody, an anti-CD28 antibody, and an isolated oligodeoxyonucleotide (ODN) having a phosphorothioate backbone, to expand the initial population of regulatory T-cells, wherein the ODN having a phosphothioate backbone is between 11 and 49 nucleotides in length, and wherein the initial population of regulatory T-cells has been enriched for CD4+CD25+CD127$^{lo}$ or CD4+CD25+ CD127− cells by obtaining a sample comprising CD4+ CD25+CD127$^{lo}$ or CD4+CD25+CD127− cells, identifying cells that are CD4+CD25+CD127$^{lo}$ or CD4+CD25+ CD127−, and collecting the identified cells to produce the initial population of regulatory T-cells enriched for CD4+ CD25+CD127$^{lo}$ or CD4+CD25+Cd127− cells.

2. The method of claim 1, wherein the stable regulatory T-cells express CD4 and at least one marker selected from the group consisting of Foxp3 and Helios.

3. The method of claim 1, wherein the isolated ODN is selected from the group consisting of an isolated ODN 21 nucleotides in length, an isolated ODN 22 nucleotides in length, an isolated ODN 23 nucleotides in length, an isolated ODN 24 nucleotides in length, and an isolated ODN 25 nucleotides in length.

4. The method of claim 1, wherein the isolated ODN is approximately 25 nucleotides length.

5. The method of claim 1, wherein the enriched population of T-cells is enriched for CD4+CD25+CD127$^{lo}$ or CD4+CD25+CD127− cells relative to the level of CD4+ CD25+CD127$^{lo}$ or CD4+CD25+CD127− cells present in blood.

6. The method of claim 1, wherein at least some of the initial regulatory T cells are Foxp3+.

7. The method of claim 6, wherein at least some of the initial regulatory T cells are also Helios+.

8. The method of claim 1, wherein at least some of the initial regulatory T cells are CD25$^{hi}$.

9. The method of claim 8, wherein at least some of the initial regulatory T-cells are Helios positive.

10. The method of claim 1, wherein expansion of the initial population of regulatory T-cells results in an expanded population of cells in which at least 60% of the cells are TSDR-demethylated, stable, regulatory T-cells.

11. A method for stabilizing T regulatory cells, the method comprising culturing an initial population of regulatory T-cells, in the presence of interleukin-2, an anti-CD3 antibody, an anti-CD28 antibody, and an isolated oligdeoxyonucleotide (ODN) having a phosphorothioate backbone, to expand the initial regulatory T-cell population, wherein the ODN having a phosphothioate backbone is between 11 and 49 nucleotides in length, and wherein the initial population of regulatory T-cells has been enriched for CD4+CD25+ CD127$^{lo}$ or CD4+CD25+CD127− cells by obtaining a sample comprising CD4+CD25+CD127$^{lo}$ or CD4+CD25+ CD127− cells, identifying cells that are CD4+CD25+ CD127$^{lo}$ or CD4+CD25+CD127−, and collecting the identified cells to produce the initial population of regulatory T-cells enriched for CD4+CD25+CD127$^{lo}$ or CD4+CD25+ Cd127− cells.

12. The method of claim 11, wherein at least some of the initial regulatory T cells are Foxp3+.

13. The method of claim 11, wherein at least some of the initial regulatory T-cells are CD25$^{hi}$.

14. The method of claim 11, wherein at least some of the initial regulatory T-cells are Helios positive.

15. The method of claim 11, wherein the enriched population of T-cells is enriched for CD4+CD25+CD127$^{lo}$ or CD4+CD25+CD127− cells relative to the level of CD4+ CD25+CD127$^{lo}$ or CD4+CD25+CD127− cells present in blood.

* * * * *